(12) United States Patent
Chopra et al.

(10) Patent No.: US 8,084,637 B2
(45) Date of Patent: Dec. 27, 2011

(54) AMIDE GELLANT COMPOUNDS WITH AROMATIC END GROUPS

(75) Inventors: Naveen Chopra, Oakville (CA); Michelle N. Chretien, Mississauga (CA); Barkev Keoshkerian, Thornhill (CA); Jennifer L. Belelie, Oakville (CA); Peter G. Odell, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 12/765,148

(22) Filed: Apr. 22, 2010

(65) Prior Publication Data

US 2011/0263890 A1    Oct. 27, 2011

(51) Int. Cl.
C07C 67/02        (2006.01)

(52) U.S. Cl. ............ 560/254; 560/130; 560/169; 554/37

(58) Field of Classification Search .................. None
See application file for complete search history.

(56) References Cited

U.S. PATENT DOCUMENTS

| | | | |
|---|---|---|---|
| 4,889,560 A | 12/1989 | Jaeger et al. | |
| 4,889,761 A | 12/1989 | Titterington et al. | |
| 5,194,638 A | 3/1993 | Frihart et al. | |
| 5,221,335 A | 6/1993 | Williams et al. | |
| 5,372,852 A | 12/1994 | Titterington et al. | |
| 5,389,958 A | 2/1995 | Bui et al. | |
| 5,621,022 A | 4/1997 | Jaeger et al. | |
| 5,783,657 A | 7/1998 | Pavlin et al. | |
| 5,998,570 A | 12/1999 | Pavlin et al. | |
| 6,111,055 A | 8/2000 | Berger et al. | |
| 6,350,889 B1 | 2/2002 | Pavlin | |
| 6,399,713 B1 | 6/2002 | MacQueen et al. | |
| 6,492,458 B1 | 12/2002 | Pavlin | |
| 7,271,284 B2 | 9/2007 | Toma et al. | |
| 7,276,614 B2 * | 10/2007 | Toma et al. ............ | 554/37 |
| 7,279,587 B2 | 10/2007 | Odell et al. | |
| 7,501,015 B2 | 3/2009 | Odell et al. | |
| 7,559,639 B2 | 7/2009 | Belelie et al. | |
| 2003/0065084 A1 | 4/2003 | MacQueen et al. | |
| 2006/0122354 A1 | 6/2006 | Carlini et al. | |
| 2006/0132570 A1 | 6/2006 | Odell et al. | |
| 2007/0012217 A1 | 1/2007 | Goredema et al. | |
| 2007/0119337 A1 | 5/2007 | Breton et al. | |
| 2007/0119338 A1 | 5/2007 | Breton et al. | |
| 2007/0119339 A1 | 5/2007 | Kovacs et al. | |
| 2007/0119340 A1 | 5/2007 | Breton et al. | |
| 2007/0120908 A1 | 5/2007 | Odell et al. | |
| 2007/0120909 A1 | 5/2007 | Belelie et al. | |
| 2007/0120910 A1 | 5/2007 | Odell et al. | |
| 2007/0120919 A1 | 5/2007 | Goredema et al. | |
| 2007/0120921 A1 | 5/2007 | Carlini et al. | |
| 2007/0120922 A1 | 5/2007 | Belelie et al. | |
| 2007/0120923 A1 | 5/2007 | Kovacs et al. | |
| 2007/0120924 A1 | 5/2007 | Odell et al. | |
| 2007/0120925 A1 | 5/2007 | Belelie et al. | |
| 2007/0123601 A1 | 5/2007 | Belelie et al. | |
| 2007/0123641 A1 | 5/2007 | Belelie et al. | |
| 2007/0123642 A1 | 5/2007 | Banning et al. | |
| 2007/0123663 A1 | 5/2007 | Toma et al. | |
| 2007/0123722 A1 | 5/2007 | Toma et al. | |
| 2007/0123723 A1 | 5/2007 | Odell et al. | |
| 2007/0123724 A1 | 5/2007 | Belelie et al. | |

FOREIGN PATENT DOCUMENTS

WO    WO 03079002 A2 *  9/2003

OTHER PUBLICATIONS

U.S. Patent Application filed Apr. 22, 2010, of Naveen Chopra et al., entitled "Phase Change Inks Containing Amide Gellant Compounds With Aromatic End Groups" 76 pages, 4 drawing sheets, U.S. Appl. No. 12/765,138, not yet published.
U.S. Patent Application filed Apr. 22, 2010, entitled "Curable Compositions For Three-Dimensional Printing," 52 pages, U.S. Appl. No. 12/765,309, not yet published.
U.S. Patent Application filed Apr. 22, 2010, entitled "Ink Compositions And Methods," 53 pages, U.S. Appl. No. 12/765,341, not yet published.
Glycosan Biosystems, "What is Photoinitiator?", http://www.glycosan.com/peg_science/what_photoinitiator.html, Aug. 31, 2011, 2 pages.
Wikipedia, "Photoinitiator", http://en.wikipedia.org/wiki/Photoinitiator, Aug. 31, 2001, 5 pages.

* cited by examiner

*Primary Examiner* — Sudhakar Katakam
(74) *Attorney, Agent, or Firm* — Marylou J. Lavoie, Esq. LLC

(57) ABSTRACT

A compound of the formula

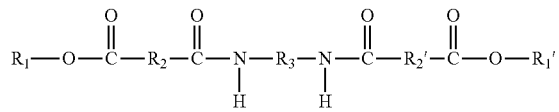

wherein $R_1$ and $R_{1'}$ are the same, and wherein $R_1$ and $R_{1'}$ are each aromatic groups; and wherein $R_2$ and $R_{2'}$ and $R_3$ each, independently of the others, are alkylene groups, arylene groups, arylalkylene groups, or alkylarylene groups; or wherein, in embodiments, $R_1$ and $R_{1'}$ can be the same or different, and wherein $R_1$ and $R_{1'}$ each, independently of the other is an alkyl group having a least one ethylenic unsaturation, an arylalkyl group having at least one ethylenic unsaturation, an alkylaryl group having at least one ethylenic unsaturation, or an aromatic group, provided that at least one of $R_1$ and $R_{1'}$ is an aromatic group; and provided that neither of $R_1$ or $R_{1'}$ is a photoinitiator group.

20 Claims, 2 Drawing Sheets

AMIDE GELLANT COMPOUNDS WITH AROMATIC END GROUPS

RELATED APPLICATIONS

Commonly assigned U.S. patent application Ser. No. 12/765,138 entitled "Phase Change Inks Containing Amide Gellant Compounds With Aromatic End Groups"), filed concurrently herewith, which is hereby incorporated by reference herein in its entirety, describes ultraviolet curable phase change inks including an amide gellant compound with aromatic end groups.

BACKGROUND

Disclosed herein are amide gellant compounds with aromatic end groups and ink compositions containing the compounds. One embodiment disclosed herein is directed to a compound of the formula

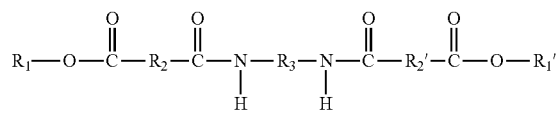

wherein $R_1$ and $R_{1'}$ are the same, and wherein $R_1$ and $R_{1'}$ each are aromatic groups; wherein $R_2$ and $R_{2'}$ are the same or different, and wherein $R_2$ and $R_{2'}$ are each independently selected from (i) alkylene groups, which can be linear or branched, saturated or unsaturated, cyclic or acyclic, substituted or unsubstituted alkylene groups, and wherein hetero atoms may optionally be present in the alkylene group; (ii) arylene groups, which can be substituted or unsubstituted arylene groups, and wherein hetero atoms may optionally be present in the arylene group; (iii) arylalkylene groups, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) alkylarylene groups, which can be substituted or unsubstituted alkylarylene groups, wherein the alkyl portion of the alkylarylene group can be linear or branched, saturated or unsaturated, cyclic or acyclic, and substituted or unsubstituted, and wherein hetero atoms may optionally be present in either the aryl portion or the alkyl portion of the alkylarylene group; and wherein $R_3$ is (i) a linear or branched alkylene group, which can be saturated or unsaturated, and substituted or unsubstituted alkylene groups, and wherein hetero atoms may optionally be present in the alkylene group; (ii) an arylene group, which can be substituted or unsubstituted arylene groups, and wherein hetero atoms may optionally be present in the arylene group; (iii) an arylalkylene group, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) an alkylarylene group, which can be substituted or unsubstituted alkylarylene groups, wherein the alkyl portion of the alkylarylene group can be linear or branched, saturated or unsaturated, cyclic or acyclic, and substituted or unsubstituted, and where hetero atoms may optionally be present in either the aryl portion or the alkyl portion of the alkylarylene group.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing.

Phase change inks for color printing typically comprise a phase change ink carrier composition which is combined with a phase change ink compatible colorant. A series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. Nos. 4,889,560, 4,889,761, and 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes.

The colorants can also include pigments, as disclosed in, for example, U.S. Pat. No. 5,221,335, the disclosure of which is totally incorporated herein by reference.

Phase change inks have also been used for applications such as postal marking, industrial marking, and labeling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

U.S. Pat. No. 7,276,614 (Eniko Toma, et al.), which is hereby incorporated by reference herein in its entirety, discloses curable ester-terminated oligoamide compounds and ink compositions containing them. Disclosed are compounds of the formula

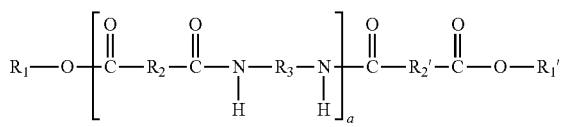

wherein $R_1$ and $R_{1'}$ each, independently of the other, is an alkyl group having at least one ethylenic unsaturation, an arylalkyl group having at least one ethylenic unsaturation, or an alkylaryl group having at least one ethylenic unsaturation, $R_2$, $R_{2'}$, and $R_3$ each, independently of the others, are alkylene groups, arylene groups, arylalkylene groups, or alkylarylene groups, and n is an integer representing the number of repeat amide units and is at least 1.

U.S. Pat. No. 7,279,587 (Peter G. Odell, et al.), which is hereby incorporated by reference herein in its entirety, discloses photoinitiating compounds compatible with or useful in phase change ink compositions. Disclosed are compounds of the formula

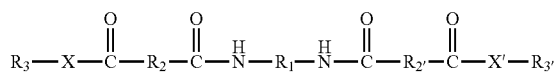

wherein $R_1$ is an alkylene, arylene, arylalkylene, or alkylarylene group, $R_2$ and $R_{2'}$ each, independently of the other, are alkylene, arylene, arylalkylene, or alkylarylene groups, $R_3$ and $R_{3'}$ each, independently of the other, are either (a) photoinitiating groups, or (b) groups which are alkyl, aryl, arylalkyl, or alkylaryl groups, provided that at least one of $R_3$ and $R_{3'}$ is a photoinitiating groups, and X and X' each, independently of the other, is an oxygen atom or a group of the formula —$NR_4$—, wherein $R_4$ is a hydrogen atom, and alkyl group, an aryl group, or an alkylaryl group.

U.S. Pat. No. 5,783,657 (Mark S. Pavlin, et al.), which is hereby incorporated by reference herein in its entirety, discloses low molecular weight, ester-terminated polyamides which may be blended with a liquid hydrocarbon to form a transparent composition having gel consistency. The ester-terminated polyamide is prepared by reacting "x" equivalents of dicarboxylic acid wherein at least 40% of those equivalents are from polymerized fatty acid, "y" equivalents of diamine such s ethylene diamine, and "z" equivalents of monoalcohol having at least 4 carbon atoms. The stoichiometry of the reaction mixture is such that $0.9 \leq \{x/(y+z)\} \leq 1.1$ and $0.1 \leq \{z/(y+z)\} \leq 0.7$. The reactants are heated until they reach reaction equilibrium. The gel contains about 5-50% ester-terminated polyamide, with the remainder preferably being pure hydrocarbon. The gels are useful in formulating personal care products and other articles wherein some degree of gel-like or self-supporting consistency is desired.

U.S. Pat. No. 6,111,055 (Vivian Berger, et al.), which is hereby incorporated by reference herein in its entirety, discloses an ester-terminated dimer acid-based polyamide may be blended with a solvent to form a gel. The solvent may be flammable, and a wick may be added to the resulting gel so as to form a candle.

While known compositions and processes are suitable for their intended purposes, a need remains for improved phase change ink compositions. In addition, a need remains for improved ultraviolet curable phase change ink compositions used in, for example, but not limited to, production printing. Further, there remains a need for an improved phase change ink composition providing wide substrate latitude, excellent adhesion, and enhanced pigment dispersion stability. Further, a need remains for gellant compositions for phase change inks that can provide enhanced spectral transmission and gelation properties. Further, there remains a need for a gellant composition for phase change inks that can be readily produced and that does not require post reaction purification to achieve the desired gellant composition. Further, there remains a need for a gellant that can provide adequate gelation strength without the need for complex processing steps. Further, there remains a need for a gellant that has high thermal stability.

The appropriate components and process aspects of the each of the foregoing U.S. patents and patent Publications may be selected for the present disclosure in embodiments thereof. Further, throughout this application, various publications, patents, and published patent applications are referred to by an identifying citation. The disclosures of the publications, patents, and published patent applications referenced in this application are hereby incorporated by reference into the present disclosure to more fully describe the state of the art to which this invention pertains.

SUMMARY

Described is a compound of the formula

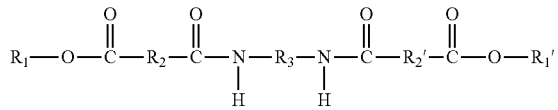

wherein $R_1$ and $R_{1'}$ are the same, and wherein $R_1$ and $R_{1'}$ each are aromatic groups;

wherein $R_2$ and $R_{2'}$ are the same or different, and wherein $R_2$ and $R_{2'}$ are each independently selected from (i) alkylene groups, which can be linear or branched, saturated or unsaturated, cyclic or acyclic, substituted or unsubstituted alkylene groups, and wherein hetero atoms may optionally be present in the alkylene group; (ii) arylene groups, which can be substituted or unsubstituted arylene groups, and wherein hetero atoms may optionally be present in the arylene group; (iii) arylalkylene groups, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) alkylarylene groups, which can be substituted or unsubstituted alkylarylene groups, wherein the alkyl portion of the alkylarylene group can be linear or branched, saturated or unsaturated, cyclic or acyclic, and substituted or unsubstituted, and wherein hetero atoms may optionally be present in either the aryl portion or the alkyl portion of the alkylarylene group; and wherein $R_3$ is (i) a linear or branched alkylene group, which can be saturated or unsaturated, and substituted or unsubstituted alkylene groups, and wherein hetero atoms may optionally be present in the alkylene group; (ii) an arylene group, which can be substituted or unsubstituted arylene groups, and wherein hetero atoms may optionally be present in the arylene group; (iii) an arylalkylene group, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) an alkylarylene group, which can be substituted or unsubstituted alkylarylene groups, wherein the alkyl portion of the alkylarylene group can be linear or branched, saturated or unsaturated, cyclic or acyclic, and substituted or unsubstituted, and where hetero atoms may optionally be present in either the aryl portion or the alkyl portion of the alkylarylene group.

Also described is a compound of the formula

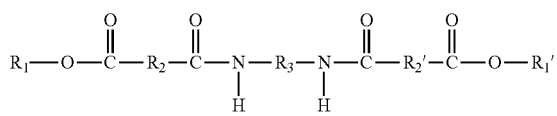

wherein $R_1$ and $R_{1'}$ can be the same or different, and wherein $R_1$ and $R_{1'}$ each, independently of the other is (i) an alkyl group having a least one ethylenic unsaturation therein, which can be linear or branched, cyclic or acyclic, and substituted or unsubstituted alkyl groups, and wherein hetero atoms may optionally be present in the alkyl group, (ii) an arylalkyl group having at least one ethylenic unsaturation therein, which can be substituted or unsubstituted arylalkyl groups, wherein the alkyl portion of arylalkyl group can be linear or branched, cyclic or acyclic, and substituted or unsubstituted, and wherein hetero atoms may optionally be present in either the aryl portion or the alkyl portion of the arylalkyl group, (iii) an alkylaryl group having at least one ethylenic unsaturation therein, which can be substituted or unsubstituted alkylaryl groups, wherein the alkyl portion of the alkylaryl group can be linear or branched, cyclic or acyclic, and substituted or unsubstituted, and wherein hetero atoms may optionally be present in either the aryl or the alkyl portion of the alkylaryl group, or (iv) an aromatic group, provided that at least one of $R_1$ and $R_{1'}$ is an aromatic group; and provided that neither of $R_1$ or $R_{1'}$ is a photoinitiator group;

wherein $R_2$ and $R_{2'}$ are the same or different, and wherein $R_2$ and $R_{2'}$ are each independently selected from (i) alkylene groups, which can be linear or branched, saturated or unsaturated, cyclic or acyclic, substituted or unsubstituted alkylene groups, and wherein hetero atoms may optionally be present in the alkylene group; (ii) arylene groups, which can be substituted or unsubstituted arylene groups, and wherein hetero atoms may optionally be present in the arylene group; (iii) arylalkylene groups, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) alkylarylene groups, which can be substituted or unsubstituted alkylarylene groups, wherein the alkyl portion of the alkylarylene group can be linear or branched, saturated or unsaturated, cyclic or acyclic, and substituted or unsubstituted, and wherein hetero atoms may optionally be present in either the aryl portion or the alkyl portion of the alkylarylene group; and wherein $R_3$ is (i) a linear or branched alkylene group, which can be saturated or unsaturated, and substituted or unsubstituted alkylene groups, and wherein hetero atoms may optionally be present in the alkylene group; (ii) an arylene group, which can be substituted or unsubstituted arylene groups, and wherein hetero atoms may optionally be present in the arylene group; (iii) an arylalkylene group, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) an alkylarylene group, which can be substituted or unsubstituted alkylarylene groups, wherein the alkyl portion of the alkylarylene group can be linear or branched, saturated or unsaturated, cyclic or acyclic, and substituted or unsubstituted, and where hetero atoms may optionally be present in either the aryl portion or the alkyl portion of the alkylarylene group.

DETAILED DESCRIPTION

Described are compounds of the formula

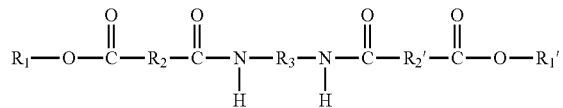

Figure 1:
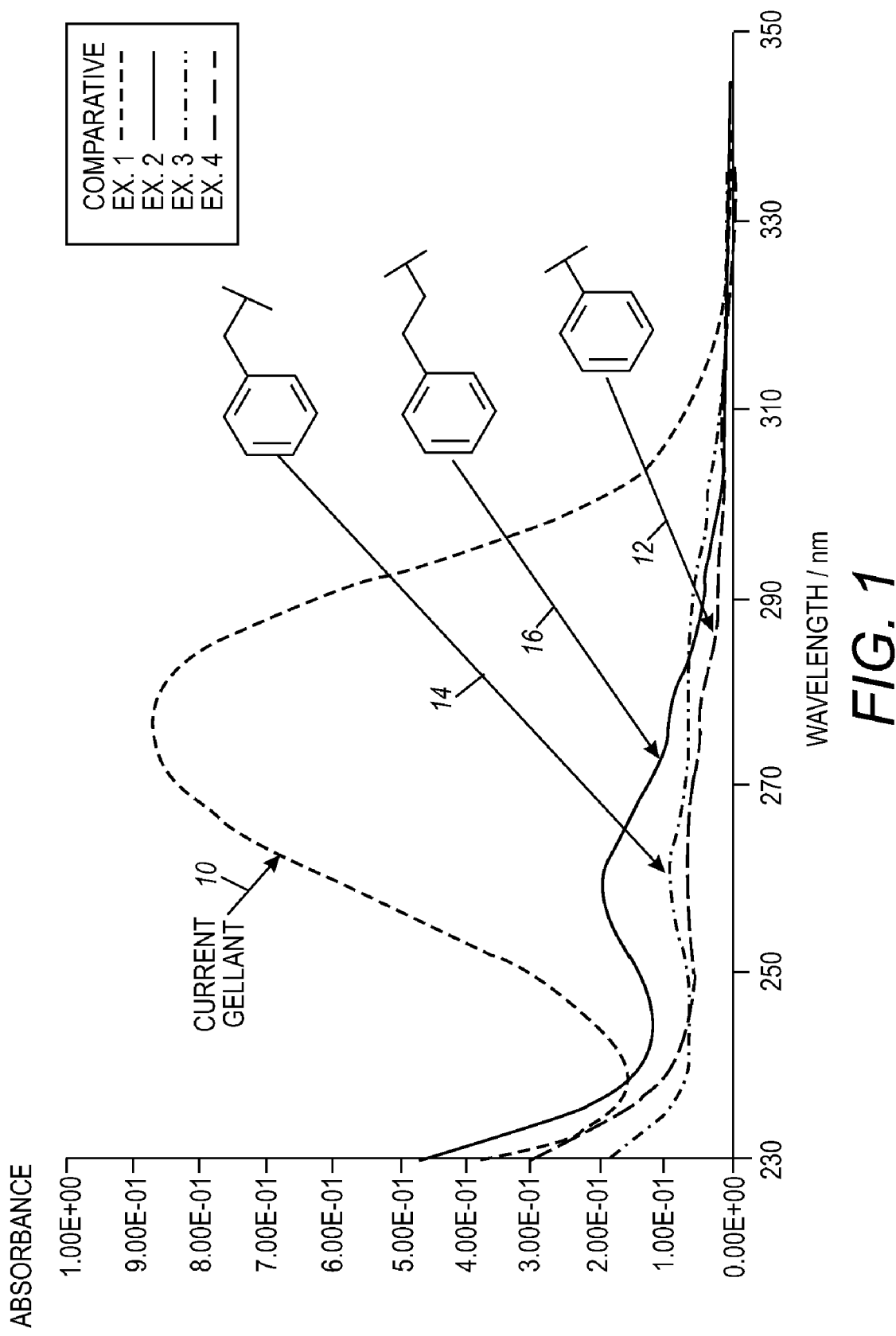
FIG. 1 is a graph showing absorbance (y-axis) versus wavelength (x-axis) for a comparative gellant and for three exemplary gellants of the present disclosure.

wherein $R_1$ and $R_{1'}$ are the same, and wherein $R_1$ and $R_{1'}$ each are an aromatic group.

In embodiments, $R_1$ and $R_{1'}$ are a single species end-capping both ends of the gellant compound which provides a single gellant product, rather than a mixture, thereby eliminating the need for complex post-reaction purification and processing. In embodiments, the gellant composition functionalized with identical aromatic end cap molecules provides enhanced spectral transmission and gelation properties. Further, in embodiments, the aromatic end capped gellant compounds have reduced ultraviolet absorbance which enables more efficient ultraviolet cure of a phase change ink prepared with the present gellants and higher ultimate viscosity providing enhanced gelation properties over prior gellant compounds. Still further, in embodiments, $R_1$ and $R_{1'}$ are the same non-reactive end cap molecule thereby providing a gellant compound having high thermal stability. With respect to thermal stability, heating of a conventional gellant overnight in an oven at 85° C. yields a product that is incompletely soluble in monomer. In embodiments herein, gellants with aromatic end-cap functionality are stable for weeks in an oven at 85° C. and the material is freely soluble in monomer. In embodiments, the gellants herein are stable for about 8 weeks in an oven held at 85° C. As used here, stable means that there is no crosslinking or decomposition of the gellant material, and it remains completely soluble in monomer. In embodiments, cleaner product synthesis with fewer side products is provided due to the use of a single end cap species.

In embodiments herein, the compounds herein provide a higher complex viscosity and increased thermal stability over prior known compounds. In certain embodiments, the compounds herein provide a complex viscosity of from about $10^4$ centipoise (cps) to about $10^8$ cps, or from about $10^5$ cps to about $10^7$ cps, or from about $10^5$ cps to about $10^6$ cps at a temperature of from about 10 to about 50° C.

In other embodiments, the compounds herein provide a reduced ultra-violet (UV) wavelength absorbance over previous known compounds which enables a more efficient UV cure of ink containing the present compounds. In certain embodiments, the compounds herein provide an absorbance of from about 0 to about 0.8, or from about 0 to about 0.7, or from about 0 to about 0.6 at a wavelength of from about 230 to about 400 nanometers. See, for example, FIG. 1, wherein the absorbance for a current gellant (Comparative Example 1) at 275 nanometers is about 8.5E-01 and the absorbance for gellants as disclosed herein at 275 nanometers is about 0.5E-01 (Example 4), about 0.75E-01 (Example 3) and about 1.00E-01 (Example 2).

In embodiments, $R_1$ and $R_{1'}$ are the same and are selected from the following aromatic groups

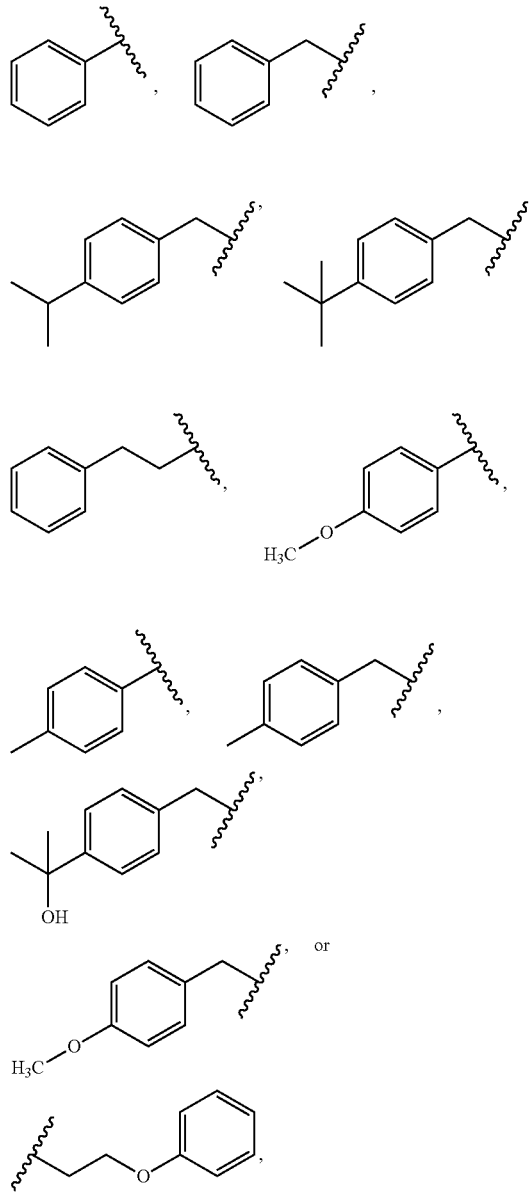

wherein ⁓⁓⁓ represents the point of attachment of the $R_1$ and $R_{1'}$ group.

In other embodiments, $R_1$ and $R_{1'}$ are the same and are selected from the formula

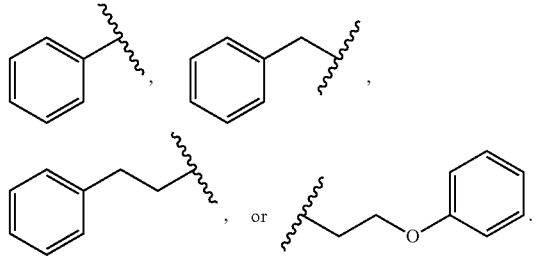

In one specific embodiment, $R_1$ and $R_{1'}$ are each of the formula

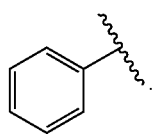

In another specific embodiment, $R_1$ and $R_{1'}$ are each of the formula

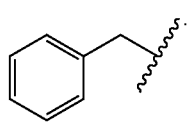

In yet another specific embodiment, $R_1$ and $R_{1'}$ are each of the formula

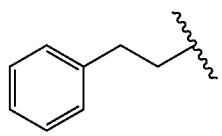

In still another specific embodiment, $R_1$ and $R_{1'}$ are each of the formula

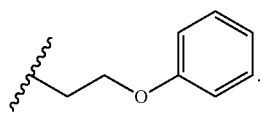

$R_2$ and $R_{2'}$ are each, independently of the other:

(i) alkylene groups (wherein an alkylene group is defined as a divalent aliphatic group or alkyl group, including linear and branched, saturated and unsaturated, cyclic and acyclic, and substituted and unsubstituted alkylene groups, and wherein hetero atoms such as oxygen, nitrogen, sulfur, silicon, phosphorus, boron, and the like, may optionally be present in the alkylene group), in embodiments, having from about 2 to about 100 carbon atoms, in embodiments having at least about 2, 4, 6, 8, 10, 12, 14, 16, 18, 20, 22, 24, 26, 28, 30, 32, 34, or 36 carbon atoms, or no more than about 100, no more than about 60, or no more than about 50 carbon atoms, and in a specific embodiment, about 36 carbon atoms, although the numbers can be outside of these ranges, (ii) arylene groups (wherein an arylene group is defined as a divalent aromatic or aryl group, including substituted and unsubstituted arylene groups, and wherein hetero atoms such as described above for the alkylene groups may optionally be present in the arylene group), in embodiments, having from about 5 to about 100 carbon atoms, in embodiments at least about 5 or 6 carbon atoms, or no more than about 100, no more than about 60, or no more than about 50 carbon atoms, although the numbers can be outside of these ranges, (iii) arylalkylene groups (wherein an arylalkylene group is defined as a divalent arylalkyl group, including substituted and unsubstituted arylalkylene groups, wherein the alkyl portion of the arylalkylene group can be linear or branched, saturated or unsaturated, cyclic or acyclic, and substituted or unsubstituted, and wherein hetero atoms such as described above for the alkylene groups may optionally be present in either the aryl portion of the alkyl portion of the arylalkylene group), in embodiments, having from about 6 to about 100 carbon atoms, in embodiments having at least about 6 or 7 carbon atoms, or nor more than about 100, no more than about 60, or no more than about 50 carbon atoms, although the numbers can be outside of these ranges, (iv) alkylarylene groups (wherein an alkylarylene group is defined as a divalent alkylaryl group, including substituted and unsubstituted alkylarylene groups, wherein the alkyl portion of the alkylarylene group can be linear or branched, saturated or unsaturated, cyclic or acyclic, and substituted or unsubstituted, and wherein hetero atoms such as described above for the alkylene groups may optionally be present in either the aryl portion or the alkyl portion of the alkylarylene group), in embodiments, having from about 6 to about 100 carbon atoms, in embodiments having at least 6 or 7 carbon atoms, or no more than about 100, no more than about 60, or no more than about 50 carbon atoms, although the numbers can be outside of these ranges, wherein the substituents on the substituted alkylene, arylene, arylalkylene, and alkylarylene groups can be, but are not limited to, the following groups: pyridine, pyridinium, ether, aldehyde, ketone, ester, amide, carbonyl, thiocarbonyl, sulfide, phosphine, phosphonium, phosphate, nitrile, mercapto, nitro, nitroso, acyl, acid anhydride, azide, azo, thiocyanato, carboxylate, urethane, urea, mixtures and combinations thereof, and the like, wherein two or more substituents can be joined together to form a ring.

In embodiments, $R_2$ and $R_{2'}$ are both alkylene groups, which can be linear or branched, saturated or unsaturated, cyclic or acyclic, and substituted alkylene groups, and hetero atoms may optionally be present in the alkylene group. In some embodiments, $R_2$ and $R_{2'}$ are both saturated alkylene groups. In other embodiments, $R_2$ and $R_{2'}$ are both unsubstituted alkylene groups. In some embodiments, $R_2$ and $R_{2'}$ are each groups of the formula $$-C_{34}H_{56+a}-$$

and are branched alkylene groups which may include unsaturations and cyclic groups, and wherein a is an integer of 0, 1, 2, 3, 4, 5, 6, 7, 8, 9, 10, 11, or 12. In specific embodiments, $R_2$ and $R_{2'}$ include isomers of the formula

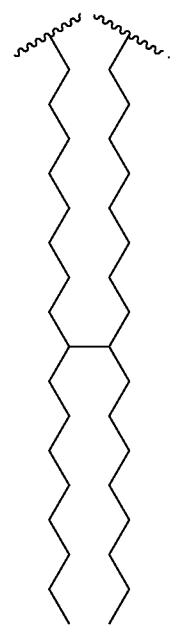

$R_3$ is (i) an alkylene group (wherein an alkylene group is defined as a divalent aliphatic group or alkyl group, including linear and branched, saturated and unsaturated, cyclic and acyclic, and substituted and unsubstituted alkylene groups, and wherein hetero atoms as described for the $R_2$ and $R_{2'}$ alkylene groups may optionally be present in the alkylene group), in embodiments, having from about 2 to about 80 carbon atoms, in embodiments, having at least about 2 carbon atoms, or no more than about 80, 60, or 50, or 36 carbon atoms, although the numbers of carbon atoms can be outside of these ranges, (ii) an arylene group (wherein an arylene group is defined as a divalent aromatic group or aryl group, including substituted and unsubstituted arylene groups, and wherein hetero atoms as described for the $R_3$ alkylene group may optionally be present in the arylene group), in embodiments, having from about 2 to about 50 carbon atoms, in embodiments about 2 carbon atoms, in further embodiments having no more than about 5 or 6 carbon atoms, or no more than about 50, 25, or 18 carbon atoms, although the numbers of carbon atoms can be outside of these ranges, (iii) an arylalkylene group (wherein an arylalkylene group is defined as a divalent arylalkyl group, including substituted and unsubstituted arylalkylene groups, wherein the alkyl portion of the arylalkylene group can be linear or branched, saturated or unsaturated, cyclic or acyclic, and substituted or unsubstituted, and wherein hetero atoms as described for the $R_3$ alkylene group may optionally be present in the either the aryl portion or the alkyl portion of the arylalkylene group), in embodiments, having from about 6 to about 50 carbon atoms, in embodiments having at least about 6 or 7 carbon atoms, or no more than about 50, 36, or 18 carbon atoms, although the numbers of carbon atoms can be outside of these ranges, (iv) an alkylarylene group (wherein an alkylarylene group is defined as a divalent alkylaryl group, including substituted and unsubstituted alkylarylene groups, wherein the alkyl portion of the alkylarylene group can be linear or branched, saturated or unsaturated, cyclic or acyclic, and substituted or unsubstituted, and wherein hetero atoms as described for the $R_3$ alkylene group may optionally be present in either the aryl portion or the alkyl portion of the alkylarylene group), in embodiments, having from about 6 to about 50 carbon atoms, in embodiments, having at least about 6 or 7 carbon atoms, or no more than about 50, 36, or 18 carbon atoms, although the numbers of carbon atoms can be outside of these ranges, wherein the substituents on the substituted alkylene, arylene, arylalkylene, and alkylarylene groups can be, but are not limited to, the following groups: pyridine, pyridinium, ether, aldehyde, ketone, ester, amide, carbonyl, thiocarbonyl, sulfide, phosphine, phosphonium, phosphate, nitrile, mercapto, nitro, nitroso, acyl, acid anhydride, azide, azo, carboxylate, urethane, urea, mixtures and combinations thereof, and the like, wherein two or more substituents can be joined together to form a ring.

In embodiments, $R_3$ is a linear or branched alkylene group, which can be saturated or unsaturated, substituted or unsubstituted alkylene groups, and wherein hetero atoms may optionally be present in the alkylene group. In a specific embodiment, $R_3$ is an ethylene group

—$CH_2CH_2$—.

In specific embodiments, the gellant compound is of the formula

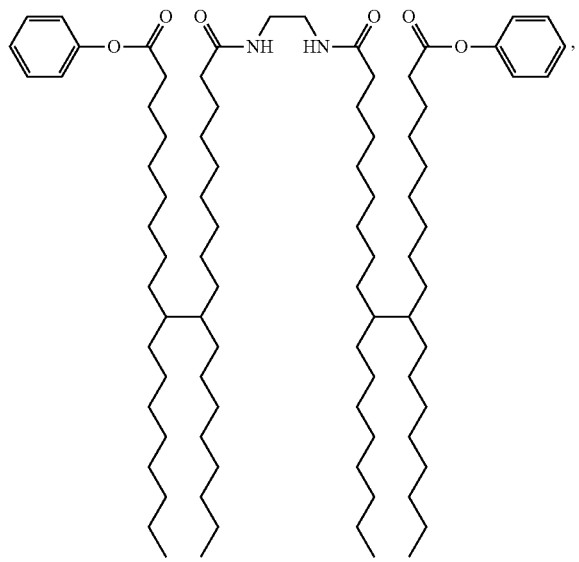,

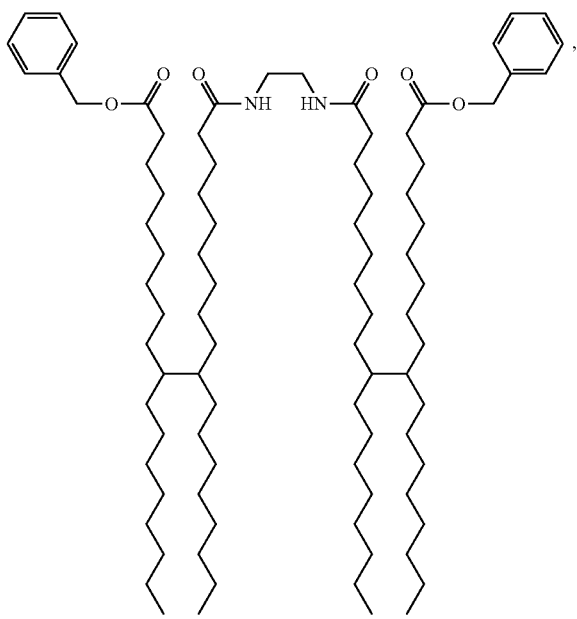,

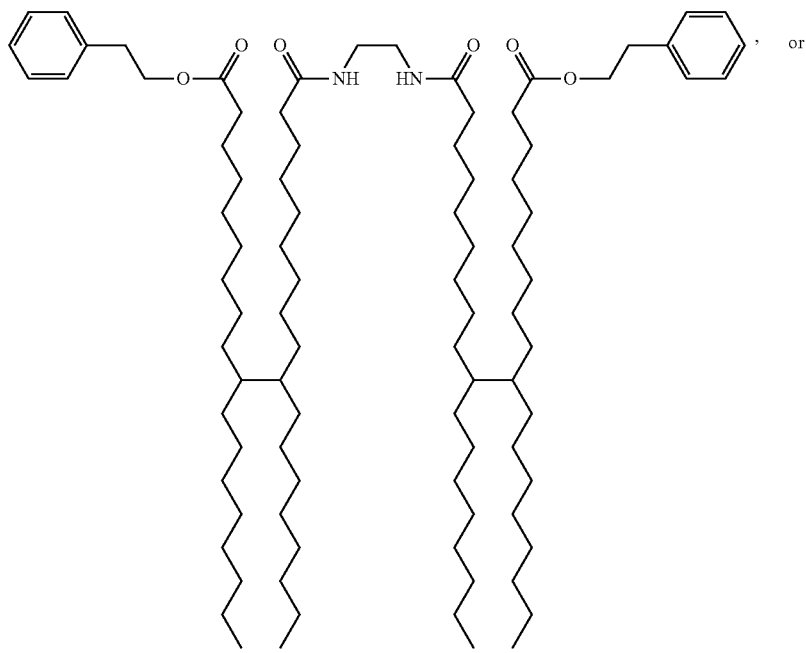 or

-continued

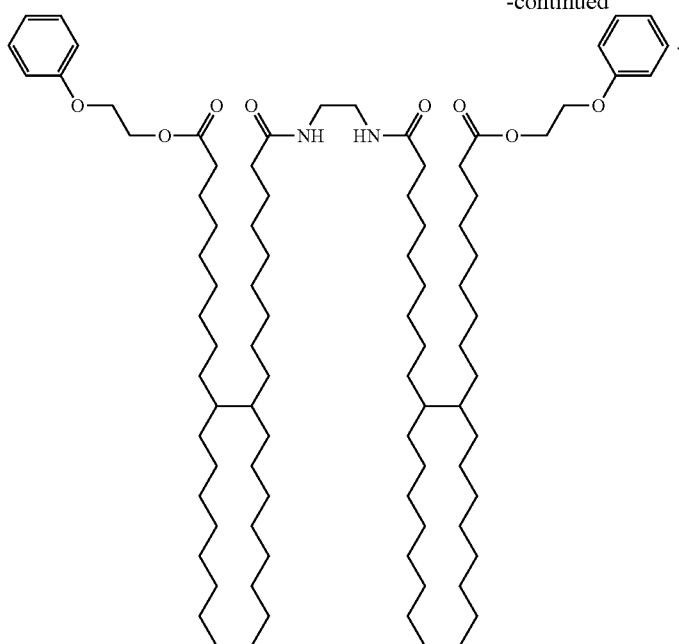

In an alternate embodiment, a compound of the formula

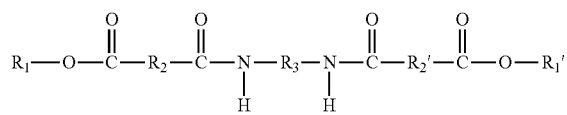

is disclosed wherein $R_2$, $R_{2'}$ and $R_3$ are as described above, and wherein $R_1$ and $R_{1'}$ can be the same or different, provided that at least one of $R_1$ and $R_{1'}$ is an aromatic group; and provided that neither of $R_1$ or $R_{1'}$ is a photoinitiator group.

In this embodiment, at least one of $R_1$ and $R_{1'}$ is an aromatic end cap comprising an aromatic group, as described herein and the other of $R_1$ or $R_{1'}$ is:

(i) an alkyl group having a least one ethylenic unsaturation therein which (including linear and branched, cyclic and acyclic, and substituted and unsubstituted alkyl groups, and wherein hetero atoms such as oxygen, nitrogen, sulfur, silicon, phosphorus, boron, and the like, may optionally be present in the alkyl group, in embodiments, having from about 2 to about 100 carbon atoms, in embodiments, having at least about 2, 3, or 4 carbon atoms, or no more than about 100, 60, or 30 carbon atoms, although the number of carbon atoms can be outside of these ranges, (ii) an arylalkyl group having at least one ethylenic unsaturation therein (including substituted and unsubstituted arylalkyl groups, wherein the alkyl portion of arylalkyl group can be linear or branched, cyclic or acyclic, and substituted or unsubstituted, and wherein hetero atoms as described above for the alkyl group may optionally be present in either the aryl portion or the alkyl portion of the arylalkyl group), in embodiments, having from about 6 to about 100 carbon atoms, in embodiments, having at least about 6 or 7 carbon atoms, or no more than about 100, 60, or 30 carbon atoms, although the number of carbon atoms can be outside of these ranges, (iii) an alkylaryl group having at least one ethylenic unsaturation therein (including substituted or unsubstituted alkylaryl groups, wherein the alkyl portion of the alkylaryl group can be linear or branched, cyclic or acyclic, and substituted or unsubstituted, and wherein hetero atoms as described above for the alkyl group may optionally be present in either the aryl portion or the alkyl portion of the alkylaryl group, in embodiments, having about 6 to about 100 carbon atoms, in embodiments, having at least about 6 or 7 carbon atoms, or not more than about 100, 60, or 30 carbon atoms, although the number of carbon atoms can be outside of these ranges, such as tolyl or the like, wherein the substituents on the substituted alkyl, arylalkyl, and alkylaryl groups can be, but are not limited to, halogen atoms and the following groups: ether, aldehyde, ketone, ester, amide, carbonyl, thiocarbonyl, sulfate, sulfonate, sulfonic acid, sulfide, sulfoxide, phosphine, phosphonium, phosphate, nitrile, mercapto, nitro, nitroso, sulfone, acyl, acid anhydride, azide, azo, cyanato, isocyanato, thiocyanato, isothiocyanato, carboxylate, carboxylic acid, urethane, urea, mixtures and combinations thereof, and the like, wherein two or more substituents can be joined together to form a ring.

In embodiments, one of $R_1$ or $R_{1'}$ is of the formula

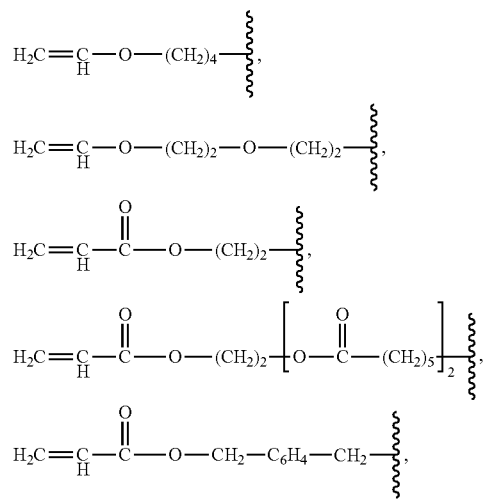

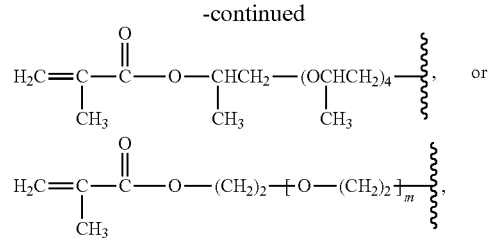 or
wherein m is an integer representing the number of repeating $(O—(CH_2)_2$ units. In embodiments, m is an integer of from about 1 to about 10, although not limited.
In specific embodiments, the gellant compound is of the formula
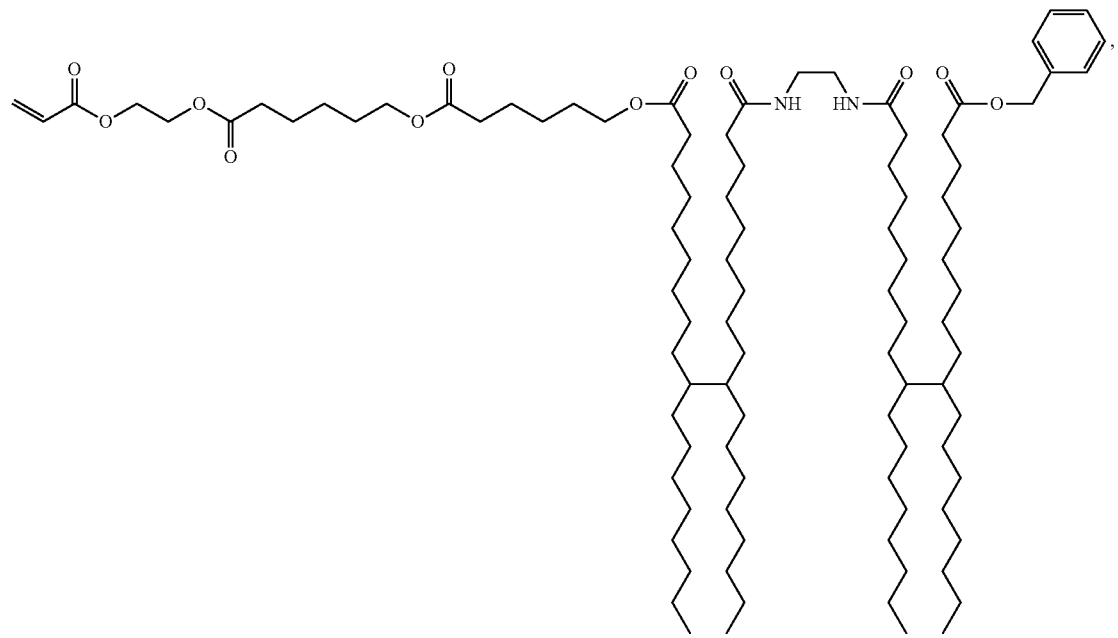
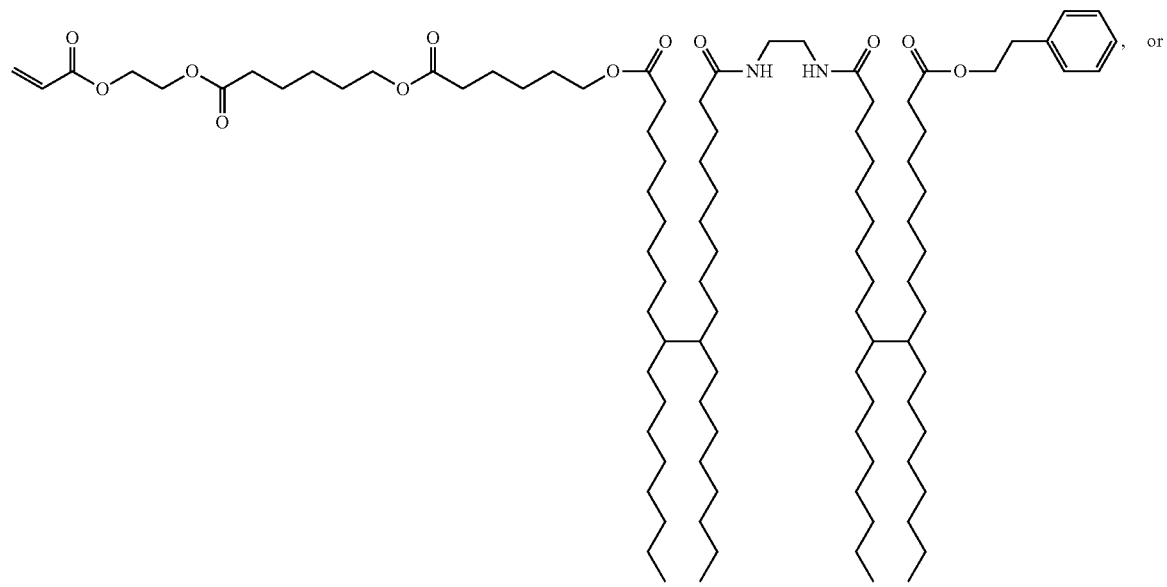

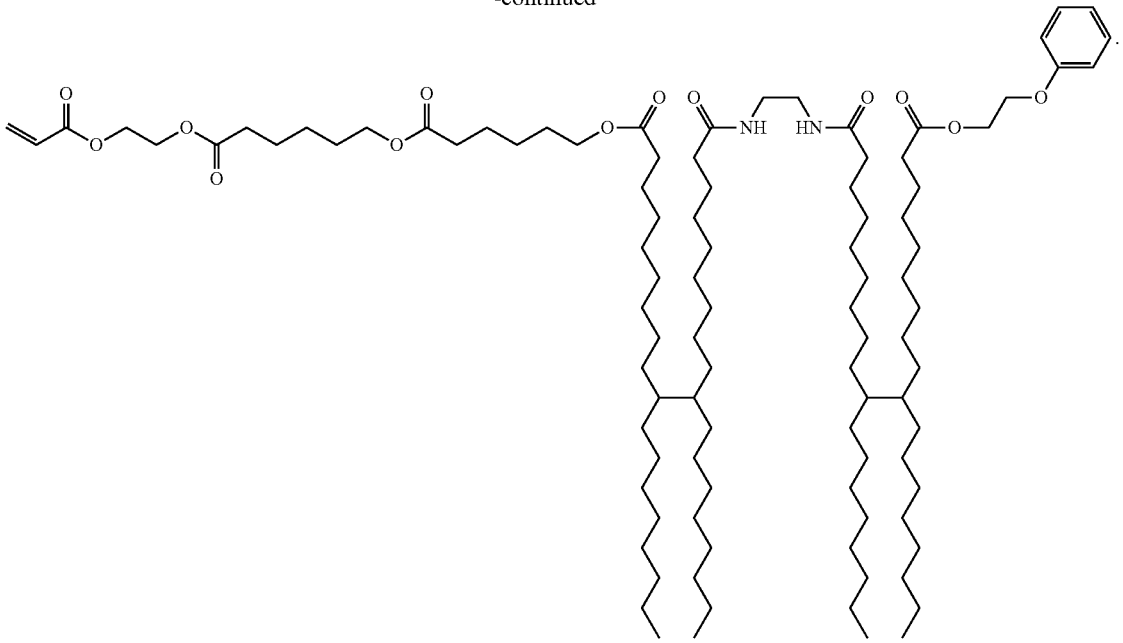

Compounds as disclosed herein can be prepared by any desired or effective method. For example, in one specific embodiment, about 2 molar equivalents of a diacid of the formula

HOOC—$R_2$—COOH and about one molar equivalent of a diamine of the formula

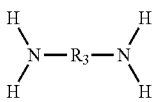

can be reacted by use of a coupling agent such as 1,3-dicyclohexylcarbodimide (DCC) in the present of a catalyst such as 4-dimethylaminopyridine (DMAP) in the presence of a solvent such as methylene chloride ($CH_2Cl_2$) at reduced temperatures followed by eventual warming to about room temperature to produce an organoamide intermediate.

The diacid and the diamine can be present in any desired or effective relative amounts. In embodiments, at least about 1.75 moles of diacid per every 1 mole of diamine, or at least about 2 moles of diacid per every 1 mole of diamine, or no more than about 2.5 moles of diacid per every 1 mole of diamine, or no more than about 2.3 moles of diacid per every 1 mole of diamine, or no more than about 2.1 moles of diacid per every 1 mole of diamine, although the relative amounts can be outside of these ranges.

In one embodiment, to the resulting reaction mixture containing the organoamide intermediate can be added about two molar equivalents of an identical aromatic end cap molecule having the formula $R_1$—OH.

In another embodiment, to the resulting reaction mixture containing the organoamide intermediate can be added about one molar equivalent of a first end cap molecule which is an aromatic alcohol having the formula $R_1$—OH as described herein and about one molar equivalent of a second end cap molecule which is an alkyl group having at least one ethylenic unsaturation, an arylalkyl group having at least one ethylenic unsaturation, or an alkylaryl group having at least one ethylenic unsaturation, as described herein. In a specific embodiment, the second end cap molecule is caprolactone acrylate.

The organoamide intermediate and the aromatic alcohol can be present in any desired or effective relative amounts. For example, wherein $R_1$ and $R_{1'}$ are the same and comprise an aromatic alcohol, in one embodiment, at least about 1.75 moles of aromatic alcohol per every 1 mole of organoamide intermediate, or at least about 2 moles of aromatic alcohol per every 1 mole of organoamide intermediate, or at least about 2.25 moles of aromatic alcohol per every 1 mole of organoamide intermediate, or no more than about 3 moles of aromatic alcohol per every 1 mole of organoamide intermediate, or no more than about 2.75 moles of aromatic alcohol per every 1 mole of organoamide intermediate, or no more than about 2.5 moles of aromatic alcohol per every 1 mole of organoamide intermediate, although the relative amounts can be outside of these ranges. In embodiments wherein $R_1$ and $R_{1'}$ are two different species, the combined total amount of $R_1$ and $R_{1'}$ is, in embodiments, at least about 1.75, 2, 2.25 moles per every 1 mole of organoamide intermediate, or no more than about 2.75 or no more than about 2.5 moles (combined total of $R_1$ and $R_{1'}$), although the relative amounts can be outside of these ranges.

The ingredients can be mixed together in the sequence just described and a one pot reaction can be employed. For example, molten organoamide intermediate can be added to a 1 liter round bottomed flask equipped with a magnetic stir bar, followed by dichloromethane solvent with stirring until the organoamide intermediate is completely dissolved to form a clear, golden solution. A catalyst, such as DMAP, can be added, followed by a coupling agent, such as DCC.

Next, in one embodiment, a single species of end cap molecule can be added to the reaction mixture containing the organoamide intermediate.

Alternately, in another embodiment, a first species of end cap molecule being an aromatic alcohol and a second species of end cap molecule that is different from the aromatic alcohol can be added simultaneously to the reaction mixture.

The reaction mixture containing the organoamide intermediate or and the single end cap component or the mixed end cap components can be allowed to stir overnight at room temperature. The reaction contents can then be filtered to remove N,N-dicyclohexylurea (DCHU) by-product. The filtrate can be concentrated on a rotary evaporator resulting in a golden gel-like solid amide gellant. The solid residue can be dried in a vacuum oven, such as for about 2 hours at about 90° C., to remove residual solvent from the amide gellant.

Examples of suitable coupling agents include 1,3-dicyclohexylcarbodiimide (DCC) of the formula

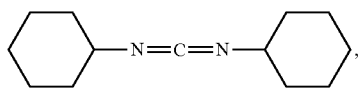

1-(3-(dimethylamino)propyl)3-ethylcarbodiimide HCl (EDCl), N,N-carbonyldiimidazole, N-cyclohexyl-N'-(2-morpholinoethyl)-carbodiimide methyl-p-toluenesulfonate, (benzotriazol-1-yloxy) tris(dimethylamino)phosphonium hexafluorophosphate (BOP), (o-benzotriazol-1-yl)-N,N,N',N'-bis(tetramethylene(uranium hexafluorophosphate (HBTU), bis(2-oxo-3-oxazolidinyl)phosphonic chloride (BOP-Cl), (1H-1,2,3-benzotriazol-1-yloxy)tris(pyrrolidino) phosphonium hexafluoro phosphate (PyBOP), and the like, and mixtures and combinations thereof.

The coupling agent and the diacid can be present in any desired or effective relative amounts. In embodiments, the coupling agent and the diacid are present in an amount of at least about 1.8 moles of coupling agent per every 1 mole of diacid, or at least about 1.9 moles of coupling agent per every 1 mole of diacid, or at least about 2 moles of coupling agent per every 1 mole of diacid, or no more than about 2.75 moles of coupling agent per every 1 mole of diacid, or no more than about 2.5 moles of coupling agent per every 1 mole of diacid, or no more than about 2.2 moles of coupling agent per every 1 mole of diacid, although the relative amounts can be outside of these ranges.

Examples of suitable catalysts include 4-dimethylaminopyridine (DMAP), of the formula

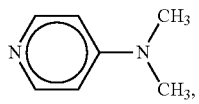

triethylamine, 1,8-diazabicyclo(4a.4.)undec-7-ene (DBU), and the like, and mixtures and combinations thereof.

The catalyst and the diacid are present in any desired or effective relative amounts. In embodiments, the catalyst and the diacid are present in an amount of at least about 0.05 mole of catalyst per every 1 mole of diacid, or at least about 0.1 mole of catalyst per every 1 mole of diacid, or at least about 0.2 mole of catalyst per every 1 mole of diacid, or no more than about 1 mole of catalyst per every 1 mole of diacid, or no more than about 0.8 mole of catalyst per every 1 mole of diacid, or no more than about 0.5 mole of catalyst per every 1 mole of diacid, although the relative amounts can be outside of these ranges.

Any desired or effective solvent can be employed. Examples of suitable solvents include methylene chloride, tetrahydrofuran, methyl ethyl ketone, toluene, dimethyl formamide, diethyl ether, hexane, ethyl acetate, and the like, and mixtures and combinations thereof.

The solvent can be present in any desired or effective amount. In embodiments the solvent can be present in an amount of at least about 10 milliliters of solvent per milimole of diacid, or at least about 15 milliliters of solvent per milimole of diacid, or at least about 20 milliliters of solvent per milimole of diacid, or no more than about 50 milliliters of solvent per milimole of diacid, or no more than about 40 milliliters of solvent per milimole of diacid, or no more than about 30 milliliters of solvent per milimole of diacid, although the amount of solvent can be outside of these ranges.

The reaction between the diacid, the diamine, and the coupling agent can be carried out at any desired or effective temperature, such as from at least about 0° C. to no more than about 50° C., or from about 5° C. to about 40° C., or from about 15° C. to about 30° C., although the temperature can be outside of these ranges.

The subsequent reaction between the resulting amine-terminated diamide intermediate and the additional diacid can be carried out at any desired or effective temperature, such as from at least about 0° C. to no more than about 50° C., or from about 5° C. to about 40° C., or from about 15° C. to about 30° C., although the temperature can be outside of these ranges.

The subsequent reaction between the resulting organoamide intermediate and the aromatic alcohol can be carried out at any desired or effective temperature, such as from at least about 15° C. to no more than about 40° C., or from about 20° C. to about 35° C., or from about 25° C. to about 30° C., although the temperature can be outside of these ranges.

The reaction between the diacid and the diamine can be carried out for any desired or effective period of time, such as for about 2 to about 5 hours, although the period of time can be outside of this range.

The reaction between the organoamide intermediate and the aromatic alcohol, or mixture of aromatic alcohol and second end cap molecule, can be carried out for any desired or effective period of time, such as from about 1.5 hours to about 12 hours, or from about 2 to about 5 hours, or from about 2.5 to about 4 hours, although the period of time can be outside of these ranges.

Subsequent to completion of the reaction, the product can be treated by any desired or effective method, such as filtration of any solid by-products or washing the solution with water depending on the coupling agent used. The solvent can be removed by rotary evaporation. If needed, the product can be purified by washing with acetone and dried in a vacuum oven.

Compounds as disclosed herein can also be prepared by first reacting about n+1 molar equivalents of a diacid of the formula

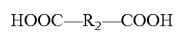

and about n molar equivalent of a diamine of the formula

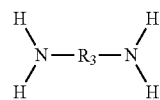

under neat conditions (i.e., in the absence of a solvent) at elevated temperatures while removing water from the reaction mixture to form an acid-terminated oligoamide of the formula

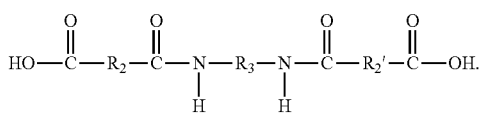

Thereafter, the acid-terminated oligoamide thus formed is reacted with about 2 molar equivalents of an aromatic alcohol of the formula $R_1$—OH or the acid-terminated organoamide thus formed is reacted with about 1 molar equivalent of an aromatic alcohol of the formula $R_1$—OH and about 1 molar equivalent of a second end cap molecule which is an alkyl group having at least one ethylenic unsaturation, an arylalkyl group having at least one ethylenic unsaturation, or an alkylaryl group having at least one ethylenic unsaturation, as described herein, by use of a coupling agent such as DCC in the presence of a catalyst such as DMAP in the presence of a solvent such as methylene chloride at reduced temperatures.

The reaction proceeds as follows:

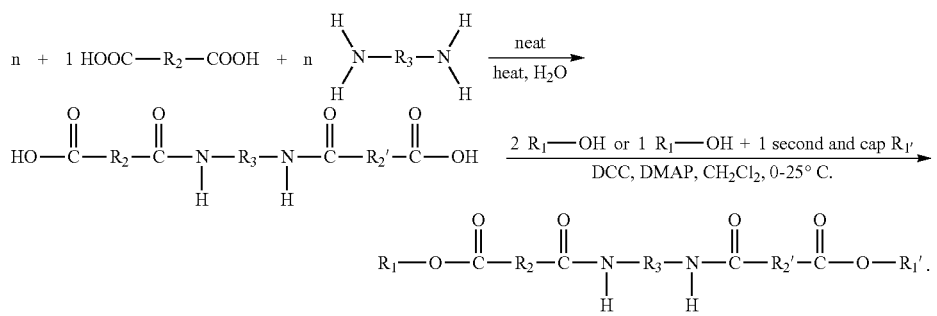

Water can be removed from the reaction mixture between the diacid and the diamine by any desired or effective method, such as by a Dean-Stark trap, molecular sieves, or other dryings agents, or the like.

The reaction between the diacid and the diamine generally is run neat, that is, in the absence of a solvent.

The reaction between the diacid and the diamine can be carried out at any desired effective temperature, such as from about 130° C. to about 180° C., or from about 140° C. to about 175° C., or from about 155° C. to about 165° C., although the temperature can be outside of these ranges.

The reaction between the diacid and the diamine can be carried out for any desired or effective period of time, such as for about 2 to about 5 hours, or from about 2.5 to about 4.5 hours, or from about 3 to about 4 hours, although the period of time can be outside of these ranges.

Thereafter, the acid-terminated organoamide intermediate and the aromatic alcohol (or mixture of aromatic alcohol and second end cap component) are reacted in the presence of a coupling agent and a catalyst.

Suitable coupling agents include those described above, such as DCC. Suitable catalysts include those described above, such as DMAP.

The acid-terminated organoamide intermediate and the aromatic alcohol (or combined total of aromatic alcohol and second end cap component) can be present in any desired or effective relative amounts, in embodiments at least 2 moles of aromatic alcohol per every 1 mole of organoamide intermediate, or no more than about 2.75 moles of aromatic alcohol per every 1 mole of organoamide intermediate, although the relative amounts can be outside of these ranges.

The acid-terminated organoamide intermediate and the coupling agent can be present in any desired or effect relative amounts, in embodiments at least about 1.8 moles of coupling agent per every 1 mole of organoamide intermediate, or no more than about 3 moles of coupling agent per every 1 mole of organoamide intermediate, although the relative amounts can be outside of these ranges.

The catalyst and the organoamide intermediate can be present in any desired or effect relative amounts, in embodiments at least about 0.05 moles of catalyst per every 1 mole of organoamide intermediate, or no more than about 0.8 moles of catalyst per every 1 mole of organoamide intermediate, although the relative amounts can be outside of these ranges.

Any desired or effective solvent can be employed including the solvents described above.

The solvent can be present in any desired or effect relative amounts, in embodiments at least about 20 milliliters of solvent per gram of organoamide intermediate, or no more than about 100 milliliters of solvent per gram of organoamide intermediate, although the amount of solvent can be outside of these ranges.

The reaction between the organoamide intermediate, the aromatic alcohol (or aromatic alcohol and second end cap component), and the coupling agent can be carried out at any desired or effective temperature, such as at least about 15° C. to about 50° C., or from about 20° C. to about 40° C., or from about 25° C. to about 35° C., although the temperature can be outside of these ranges.

The reaction between the acid-terminated organoamide intermediate, the aromatic alcohol (or aromatic alcohol and second end cap component), can be carried out for any desired or effective period of time, such as from about 2 hours to about 12 hours, or from about 2 to about 5 hours, or from about 2.5 to about 4 hours, although the period of time can be outside of these ranges.

Subsequent to completion of the reaction, the product can be treated by any desired or effective method, such as filtration of any solid by-products or washing the solution with water depending on the coupling agent used. The solvent can be removed by rotary evaporation. If needed, the product can be purified by washing with acetone and dried in a vacuum oven.

Many embodiments of the compounds thus prepared can exhibit gel-like behavior when present in solutions. Examples of materials in which the present compounds can be dissolved include curable monomers such as, for example, propoxylated neopentyl glycol diacrylate, such as SR9003®, commercially available from Sartomer Co. Inc. By gel-like behavior is meant that they undergo a relatively sharp increase in viscosity over a relatively narrow temperature range. In embodiments, some compounds as disclosed herein undergo a change in viscosity of at least about $10^3$ centipoise, at least about $10^5$ centipoise, or at least about $10^6$ centipoise, over a temperature range of at least about 5° C., at least about 10° C., or at least about 30° C., although the viscosity change and the temperature range can be outside of these ranges, and compounds that do not undergo changes within these ranges are also included herein.

At least some embodiments of the compounds disclosed herein can form a semi-solid gel at a first temperature. For example, when the compound is incorporated into a phase change ink, this temperature is below the specific temperature at which the ink is jetted. The semi-solid gel phase is a physical gel that exists as a dynamic equilibrium comprising one or more solid gellant molecules and a liquid solvent. The semi-solid gel phase is a dynamic networked assembly of molecular components held together by non-covalent interactions such as hydrogen bonding, van der Waals interactions, aromatic non-bonding interactions, ionic or coordination bonding, London dispersion forces, or the like, which, upon stimulation by physical forces, such as temperature, mechanical agitation, or the like, or chemical forces such as pH, ionic strength, or the like, can undergo reversible transitions from liquid to semi-solid state at the macroscopic level. The solutions containing the gellant molecules exhibit a thermally reversible transition between the semi-solid gel state and the liquid state when the temperature is varied above or below the gel point of the solution. This reversible cycle of transitioning between semi-solid gel phase and liquid phase can be repeated many times in the solution formulation.

In embodiments, the compounds disclosed herein are curable. "Curable" as used herein means polymerizable or chain extendable, that is, a material that can be cured via polymerization, including, but not limited to, free radical polymerization or chain extension, cationic polymerization or chain extension, and/or in which polymerization is photoinitiated through use of a radiation sensitive photoinitiator. Radiation curable as used herein is intended to cover all forms of curing upon exposure to a radiation source, including, but not limited to, light and heat sources and including in the presence or absence of initiators. Examples of radiation curing include, but are not limited to, ultraviolet (UV) light, for example having a wavelength of from about 200 to about 400 nanometers, visible light, or the like, optionally in the presence of photoinitiators and/or sensitizers, electron-beam radiation, optionally in the presence photoinitiators, thermal curing, optionally in the presence of high temperature thermal initiators (and which are in selected embodiments largely inactive at the jetting temperature when used in phase change inks), and appropriate combinations thereof.

EXAMPLES

The following Examples are being submitted to further define various species of the present disclosure. These Examples are intended to be illustrative only and are not intended to limit the scope of the present disclosure. Also, parts and percentages are by weight unless otherwise indicated.

Preparation of organoamide precursor. An organoamide precursor was prepared as follows. To a 4 liter kettle equipped with a heating mantle, overhead stirrer with PTFE (polytetrafluoroethylene) paddle, 250 milliliter dropping funnel, Dean-Stark trap and reflux condenser was added Pripol® C36 dimer diacid (acid#196, 2 equivalents, 4.23 moles, 2,422 grams, available from Cognis Corporation) followed by Irgafos® 168 (0.2 weight %, 5.1 grams, 7.9 millimoles, available from BASF Corporation). The viscous solution was heated to 90° C., purged with Argon and stirred. Next, ethylene diamine (1 equivalent, 2.11 moles, 141.4 milliliters, obtained from Sigma-Aldrich Fine Chemicals) was charged into the dropping funnel and added dropwise to the kettle over 1 hour. After addition was complete, the kettle was heated to 155° C., and held at this temperature for 3 hours. During this time, the water condensate was collected in the Dean-Stark trap. After 3 hours' time, the reaction product was a viscous golden syrup. The reaction was stopped, and the molten product was discharged into foil pans to cool to room temperature. 2,205 grams of organoamide product was isolated as a tacky, amber resin. Acid#: 92.23, amine#: 1.64. The organoamide precursor was used in the following examples.

Comparative Example 1

A conventional gellant compound was prepared as follows. 331 grams of molten organoamide precursor described above (285 millimoles, 1 equivalent) were added to a 5 liter round bottomed flask equipped with a magnetic stir bar. Next, 3.6 liters of dichloromethane were added, and the mixture was stirred until all of the organoamide was dissolved. Next, 4,4-dimethylaminopyridine (7.0 grams, 57.3 millimoles, 0.20 equivalent) was added, followed by addition of 1,3-dicyclohexylcarbodiimide (141.95 grams, 688 millimoles, 2.4 equivalents). After 15 minutes, a cloudy suspension formed. To the suspension were added Irgacure® 2959 (64.22 grams, 286 millimoles, 1 equivalent) and SR495B® caprolactone acrylate (98.39 grams, 286 millimoles, 1 equivalent), and the reaction was allowed to stir overnight at room temperature. The next day, the reaction mixture was filtered to remove N,N-dicyclohexylurea (byproduct) and the filtrate solvent was removed in vacuo to yield an off-white, opaque solid. The solid residue was reslurried in 2 liters of acetone with stirring for 2 hours, then re-filtered to give a rubbery solid. The solid residue was dried in a vacuum oven for 2 hours at 90° C. to remove residual solvent, to furnish 410 grams (242 millimoles, 85% yield) of conventional gellant product as a translucent gel whose major component is believed to be of the formula

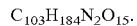

$C_{103}H_{184}N_2O_{15}$.

It is noted that the Pripol® starting material in step 1 is a product mixture, and is 'mostly' dimer acid. As a consequence, the organoamide and gellant are also mixtures. Moreover, the organoamide can have some oligomeric content.

$^1$H NMR (ppm, CDCl$_3$, 300 MHz, room temperature): δ 8.08 (2H, d, J=9 Hz, ArH), 6.97 (2H, d, J=9 Hz, ArH), 6.45 (1H, d, J=17 Hz, CH$_2$=CHC(O)), 6.15 (1H, dd, J=18 Hz, 10.5 Hz, CH$_2$=CHC(O)), 5.88 (1H, d, J=10.5 Hz, CH$_2$=CHC(O)), 4.46 (2H, m, CH$_2$O), 4.35 (4H, m, CH$_2$O), 4.26 (2H, m, CH$_2$O), 4.07 (4H, m, CH$_2$O), 3.01 (4H, br, NHCH$_2$CH$_2$NH) 2.33 (8H, m, α-CH$_2$ (esters)), 2.18 (4H, t, J=7.2 Hz, α-CH$_2$ (amide)), 1.62-0.88 (br, aliphatic H).

Example 2

A phenethyl gellant compound was prepared as follows. 68.61 grams of molten organoamide precursor described above (59.3 millimoles, 1 equivalent) were added to a 1 liter round bottomed flask equipped with a magnetic stir bar. Next, 350 milliliters of dichloromethane were added, and the mixture was stirred until all of the organoamide was dissolved. Next, 4,4-dimethylaminopyridine (1.086 grams, 8.89 millimoles, 0.15 equivalent) was added, followed by addition of 1,3-dicyclohexylcarbodiimide (29.3 grams, 142 millimoles, 2.4 equivalents). After 15 minutes, a cloudy suspension formed. To the suspension was added 2-phenethyl alcohol (14.48 grams, 119 millimoles, 2 equivalents), and the reaction was allowed to stir overnight at room temperature. The next day, the reaction mixture was filtered to remove N,N-dicyclohexylurea (by-product) and the filtrate solvent was removed in vacuo to yield an off-white, opaque solid. The solid residue was dried in a vacuum oven for 2 hours at 90° C. to remove residual solvent, to furnish 61.27 grams (44.8 millimoles, 76% yield) of phenethyl gellant product as a translucent gel believed to be of the formula

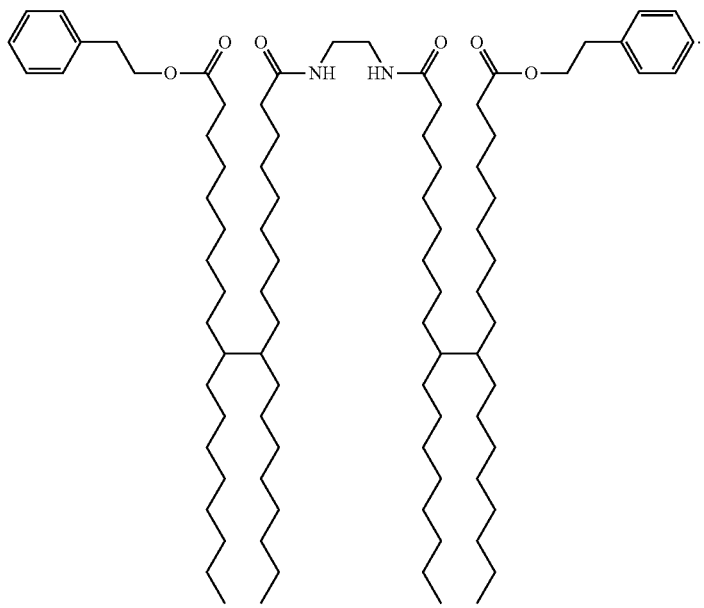

$^1$H NMR (ppm, CDCl$_3$, 300 MHz, room temperature): δ 7.27 (10H, m, ArH), 4.30 (4H, t, J=7.2 Hz, ArCH$_2$CH$_2$O), 3.39 (4H, br, NHCH$_2$CH$_2$NH), 2.95 (4H, t, J=7 Hz, ArCH$_2$) 2.5, (2H, br, NH), 2.28 (4H, t, J=7.5 Hz, α-CH$_2$ (ester)), 2.19 (4H, t, J=7.5 Hz, α-CH$_2$ (amide)), 1.62-0.88 (br, aliphatic H).

Example 3

A benzyl gellant compound was prepared as follows. 57.84 grams of molten organoamide precursor described above (50 millimoles, 1 equivalent) were added to a 1 liter round bottomed flask equipped with a magnetic stir bar. Next, 350 milliliters of dichloromethane were added, and the mixture was stirred until all of the organoamide was dissolved. Next, 4,4-dimethylaminopyridine (0.915 grams, 7.49 millimoles, 0.15 equivalent) was added, followed by addition of 1,3-dicyclohexylcarbodiimide (24.73 grams, 120 millimoles, 2.4 equivalents). After 15 minutes, a cloudy suspension formed. To the suspension was added benzyl alcohol (5.4 grams, 50 millimoles, 1.0 equivalent), and the reaction was allowed to stir overnight at room temperature. The next day, the reaction was filtered to remove N,N-dicyclohexylurea (byproduct) and the filtrate solvent was removed in vacuo to yield an off-white, opaque solid. The solid residue was dried in a vacuum oven for 2 hours at 90° C. to remove residual solvent, to furnish 67.51 grams (50.4 millimoles, 101% yield) of benzyl gellant product as a translucent gel believed to be of the formula

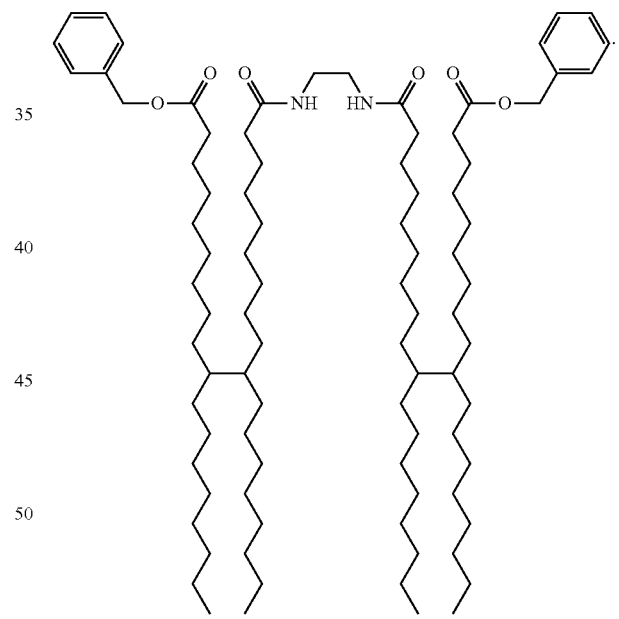

$^1$H NMR (ppm, CDCl$_3$, 300 MHz, room temperature): δ 7.36 (10H, m, ArH), 5.13 (4H, s, ArCH$_2$), 3.38 (4H, br, NHCH$_2$CH$_2$NH), 2.28 (4H, t, J=7.5 Hz, α-CH$_2$ (ester)), 2.18 (4H, t, J=7.5 Hz, α-CH$_2$ (amide)), 1.62-0.88 (br, aliphatic H).

Example 4

A phenol gellant compound was prepared as follows. 15.28 grams of molten organoamide precursor described above (acid number: 97.16, $n_{acid}$=26.46 millimoles, 1 equivalent) were added to a 250 milliliter round bottomed flask equipped with a magnetic stir bar. Next, 150 milliliters of dichloromethane were added, and the mixture was stirred until all of the organoamide was dissolved. Next, 4,4-dimethylaminopyridine (323 milligrams, 0.1 millimole) was added, followed by addition of 1,3-dicyclohexylcarbodiimide (6.55 grams, 31.75 millimoles, 1.2 equivalents). After 15 minutes, a cloudy suspension formed. To the suspension was added phenol (2.49 grams, 1.0 equivalent), and the reaction was allowed to stir overnight at room temperature. The next day, the reaction was filtered to remove N,N-dicyclohexylurea (by-product) and the filtrate solvent was removed in vacuo to yield an off-white, opaque solid. The solid residue was dried in a vacuum oven for 2 hours at 90° C. to remove residual solvent, to furnish 11.3 grams (17.2 millimoles, 65%) of gellant product as a translucent gel believed to be of the formula

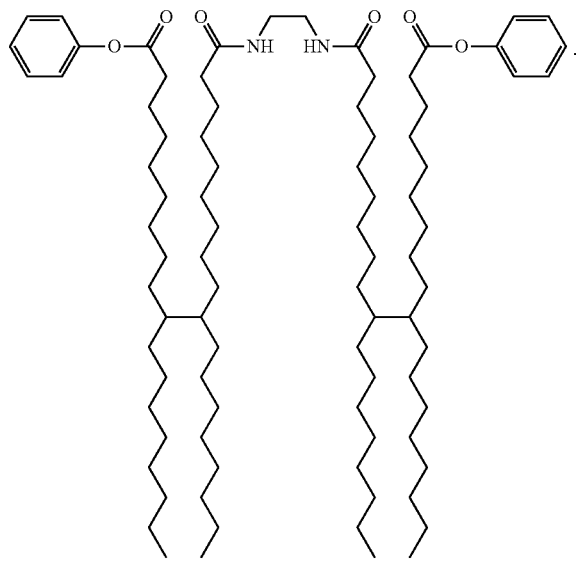

$^1$H NMR (ppm, CDCl$_3$, 300 MHz, room temperature): δ 7.41-7.08 (10H, m, ArH), 3.36 (4H, br, NHCH$_2$CH$_2$NH), 2.60 (4H, t, J=7.5 Hz, α-CH$_2$ (ester)), 2.18 (4H, t, J=7.5 Hz, α-CH$_2$ (amide)), 1.95-0.85 (br, aliphatic H).

Example 5

A phenyl glycol gellant compound was prepared as follows. 64.06 grams of molten organoamide precursor described above (55.3 millimoles, 1 equivalent) were added to a 1 liter round bottomed flask equipped with a magnetic stir bar. Next, 350 milliliters of dichloromethane were added, and the mixture was stirred until all of the organoamide was dissolved. Next, 4,4-dimethylaminopyridine (1.014 grams, 8.30 millimoles, 0.15 equivalent) was added, followed by addition of 1,3-dicyclohexylcarbodiimide (27.4 grams, 133 millimoles, 2.4 equivalents). After 15 minutes, a cloudy suspension formed. To the suspension was added phenyl glycol (15.29 grams, 111 millimoles, 2 equivalents), and the reaction was allowed to stir overnight at room temperature. The next day, the reaction mixture was filtered to remove N,N-dicyclohexylurea (by-product) and the filtrate solvent was removed in vacuo to yield an off-white, opaque solid. The solid residue was dried in a vacuum oven for 2 hours at 90° C. to remove residual solvent, to furnish 41.5 grams (29.7 millimoles, 53.6% yield) of phenyl glycol gellant product as a translucent gel believed to be of the formula

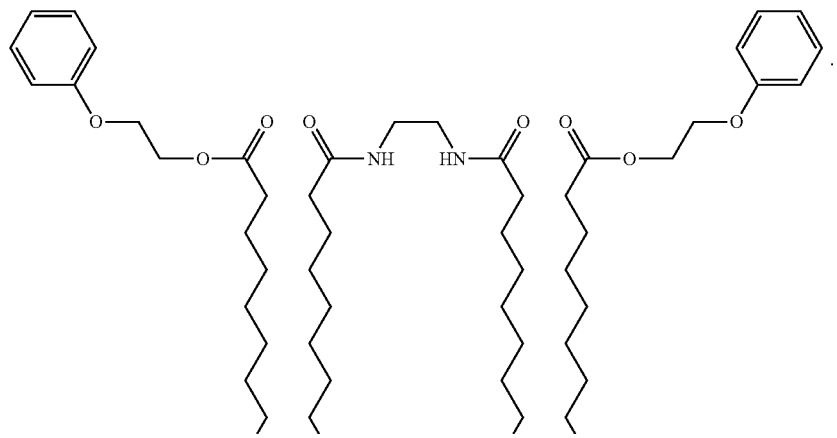

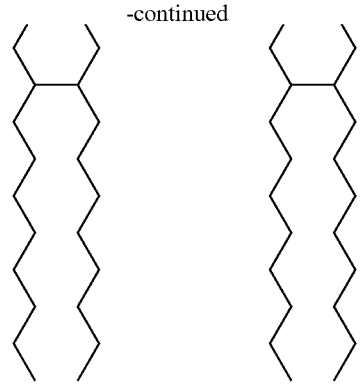

¹H NMR (ppm, CDCl₃, 300 MHz, room temperature): δ 7.31 (4H, m, ArH), 6.94 (6H, m, ArH), 4.44 (4H, J=4.8 Hz, ArOCH2), 4.19 (4H, t, J=5.1 Hz, ArOCH$_2$CH$_2$), 3.38 (4H, br, NHCH$_2$CH$_2$NH), 2.36 (4H, t, J=7.5 Hz, α-CH2 (ester)), 2.19 (4H, t, J=7.5 Hz, α-CH$_2$ (amide)), 1.95-0.85 (br, aliphatic H).

Example 6

A mixed benzyl gellant compound was prepared as follows. 54.6 grams of molten organoamide precursor described above (47.2 millimoles, 1 equivalent) were added to a 1 liter round bottomed flask equipped with a magnetic stir bar. Next, 350 milliliters of dichloromethane were added, and the mixture was stirred until all of the organoamide was dissolved. Next, 4,4-dimethylaminopyridine (0.864 grams, 7.07 millimoles, 0.15 equivalent) was added, followed by addition of 1,3-dicyclohexylcarbodiimide (23.35 grams, 113 millimoles, 2.4 equivalents). After 15 minutes, a cloudy suspension formed. To the suspension was added benzyl alcohol (5.1 grams, 47.2 millimoles, 1.0 equivalent) and caprolactone acrylate (SR495B® available from Sartomer Corporation, 16.26 grams, 47.2 millimoles, 1.0 equivalent), and the reaction was allowed to stir overnight at room temperature. The next day, the reaction was filtered to remove N,N-dicyclohexylurea (by-product) and the filtrate solvent was removed in vacuo to yield an off-white, opaque solid. The solid residue was dried in a vacuum oven for 2 hours at 90° C. to remove residual solvent, to furnish 64.7 grams (41.1 millimoles, 87% yield) of mixed benzyl gellant product as a translucent gel believed to be of the formula

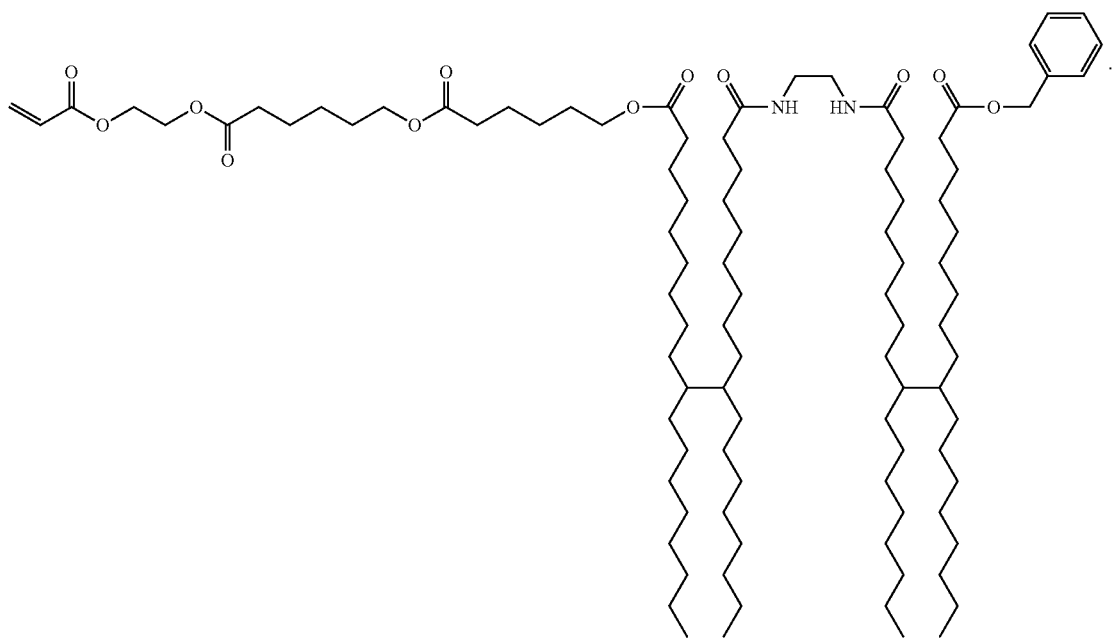

¹H NMR (ppm, CDCl₃, 300 MHz, room temperature): δ 7.36 (5H, m, ArH), 6.44 (1H, d, J=15.6 Hz, CH$_2$=CHC(O)), 6.18 (1H, m, CH$_2$=CHC(O)), 5.87 (1H, d, J=10.2 Hz, CH$_2$=CHC(O)), 5.12 (2H, s, ArCH$_2$), 4.35 (4H, m, CH$_2$O), 4.07 (4H, t, J=7 Hz, CH$_2$O), 3.38 (4H, br, NHCH$_2$CH$_2$NH), 2.33 (4H, t, J=7.5 Hz, α-CH$_2$ (ester)), 2.18 (4H, t, J=7.5 Hz, α-CH$_2$ (amide)), 1.95-0.85 (br, aliphatic H).

Example 7

A mixed phenethyl gellant compound was prepared as follows. 66.58 grams of molten organoamide precursor described above (57.5 millimoles, 1 equivalent) were added to a 1 liter round bottomed flask equipped with a magnetic stir bar. Next, 350 milliliters of dichloromethane were added, and the mixture was stirred until all of the organoamide was dissolved. Next, 4,4-dimethylaminopyridine (1.054 grams, 8.62 millimoles, 0.15 equivalent) was added, followed by addition of 1,3-dicyclohexylcarbodiimide (28.5 grams, 138 millimoles, 2.4 equivalents). After 15 minutes, a cloudy suspension formed. To the suspension was added 2-phenylethyl alcohol (7.02 grams, 57.5 millimoles, 1.0 equivalent) and caprolactone acrylate (SR495B® available from Sartomer Corporation, 16.26 grams, 47.2 millimoles, 1.0 equivalent), and the reaction was allowed to stir overnight at room temperature. The next day, the reaction was filtered to remove N,N-dicyclohexylurea (by-product) and the filtrate solvent was removed in vacuo to yield an off-white, opaque solid. The solid residue was dried in a vacuum oven for 2 hours at 90° C. to remove residual solvent, to furnish 82 grams (51.6 millimoles, 90% yield) of mixed benzyl gellant product as a translucent gel believed to be of the formula

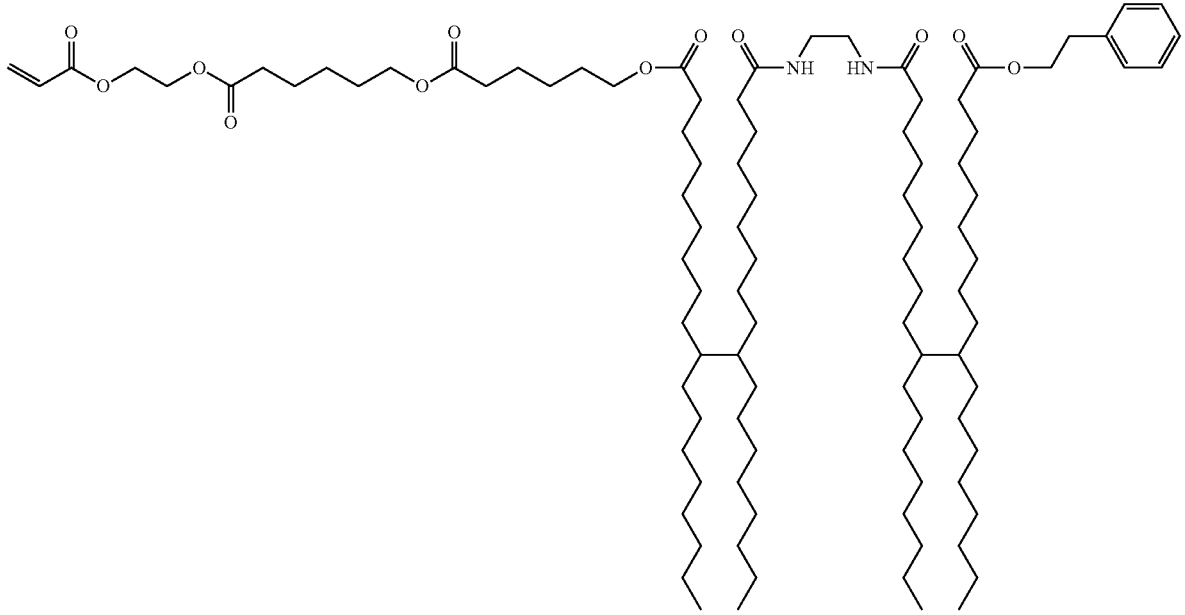

$^1$H NMR (ppm, CDCl$_3$, 300 MHz, room temperature): δ 7.29-7.22 (5H, m, ArH), 6.45 (1H, d, J=17 Hz, CH$_2$=CHC (O)), 6.16 (1H, m, CH$_2$=CHC(O)), 5.88 (1H, d, J=10.5 Hz, CH$_2$=CHC(O)), 4.35 (4H, m, CH$_2$O), 4.07 (4H, t, J=7 Hz, CH$_2$O), 3.38 (4H, br, NHCH$_2$CH$_2$NH), 2.33 (4H, t, J=7.5 Hz, α-CH$_2$ (ester)), 2.18 (4H, t, J=7.5 Hz, α-CH$_2$ (amide)), 1.95-0.85 (br, aliphatic H).

Example 8

A mixed phenyl glycol gellant compound was prepared as follows. 66.13 grams of molten organoamide precursor described above (57.1 millimoles, 1 equivalent) were added to a 1 liter round bottomed flask equipped with a magnetic stir bar. Next, 350 milliliters of dichloromethane were added, and the mixture was stirred until all of the organoamide was dissolved. Next, 4,4-dimethylaminopyridine (1.047 grams, 8.57 millimoles, 0.15 equivalent) was added, followed by addition of 1,3-dicyclohexylcarbodiimide (28.3 grams, 137 millimoles, 2.4 equivalents). After 15 minutes, a cloudy suspension formed. To the suspension was added phenyl glycol (7.89 grams, 57.1 millimoles, 1.0 equivalent) and caprolactone acrylate (SR495B® available from Sartomer Corporation, 16.26 grams, 47.2 millimoles, 1.0 equivalent), and the reaction was allowed to stir overnight at room temperature. The next day, the reaction was filtered to remove N,N-dicyclohexylurea (byproduct) and the filtrate solvent was removed in vacuo to yield an off-white, opaque solid. The solid residue was dried in a vacuum oven for 2 hours at 90° C. to remove residual solvent, to furnish 78.83 grams (49.1 millimoles, 86% yield) of mixed phenyl glycol gellant product as a translucent gel believed to be of the formula

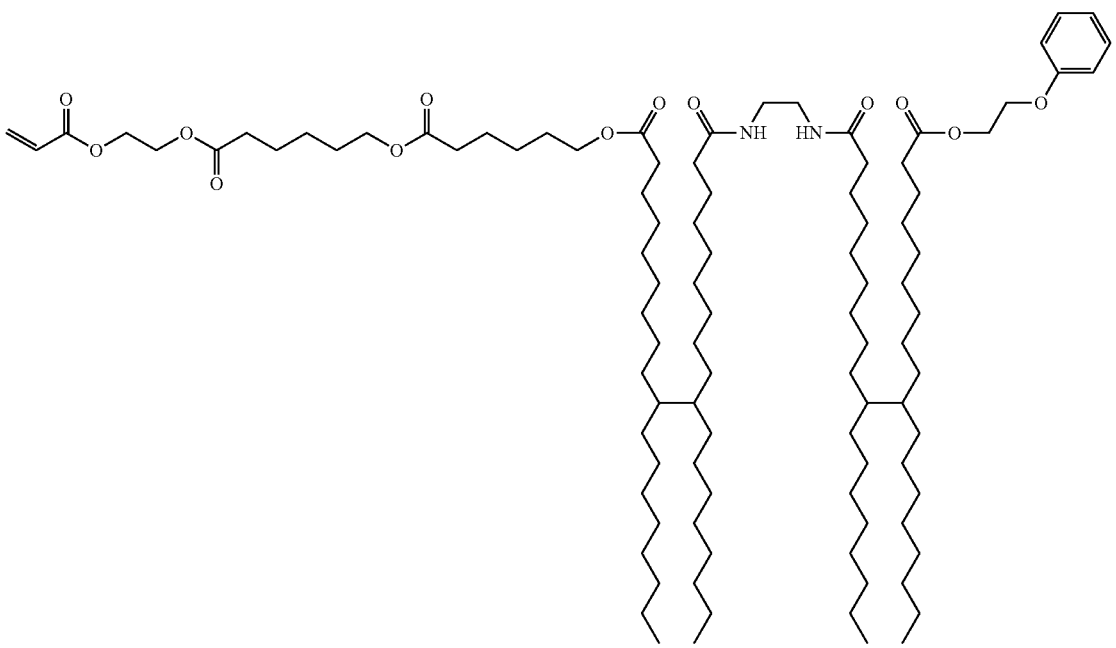

$^1$H NMR (ppm, CDCl$_3$, 300 MHz, room temperature): δ 7.28-6.95 (5H, m, ArH), 6.45 (1H, d, J=17 Hz, CH$_2$=CHC(O)), 6.18 (1H, dd, J=18 Hz, 10.5 Hz, CH$_2$=CHC(O)), 6.12 (1H, d, J=10.5 Hz, CH$_2$=CHC(O)), 4.44 (2H, m, CH$_2$CH$_2$O), 4.35 (4H, m, CH$_2$O), 4.18 (2H, m, CH$_2$O), 4.07 (4H, t, J=7 Hz, CH$_2$O), 3.38 (4H, br, NHCH$_2$CH$_2$NH), 2.33 (4H, t, J=7.5 Hz, α-CH$_2$ (ester)), 2.18 (4H, t, J=7.5 Hz, α-CH$_2$ (amide)), 1.95-0.85 (br, aliphatic H).

Ultraviolet/visible spectral comparison of some of the gellants disclosed herein were obtained using a Cary spectrophotometer. All samples were prepared at concentrations of 0.2 mg/mL in dichloromethane. FIG. 1 shows absorbance (y-axis) versus wavelength (x-axis, nanometers) for Comparative gellant Example 1 (line 10), Example 2 (phenethyl gellant, line 16), Example 3 (di-benzyl gellant, line 14, and Example 4 (phenol gellant, line 12).

Figure 2:
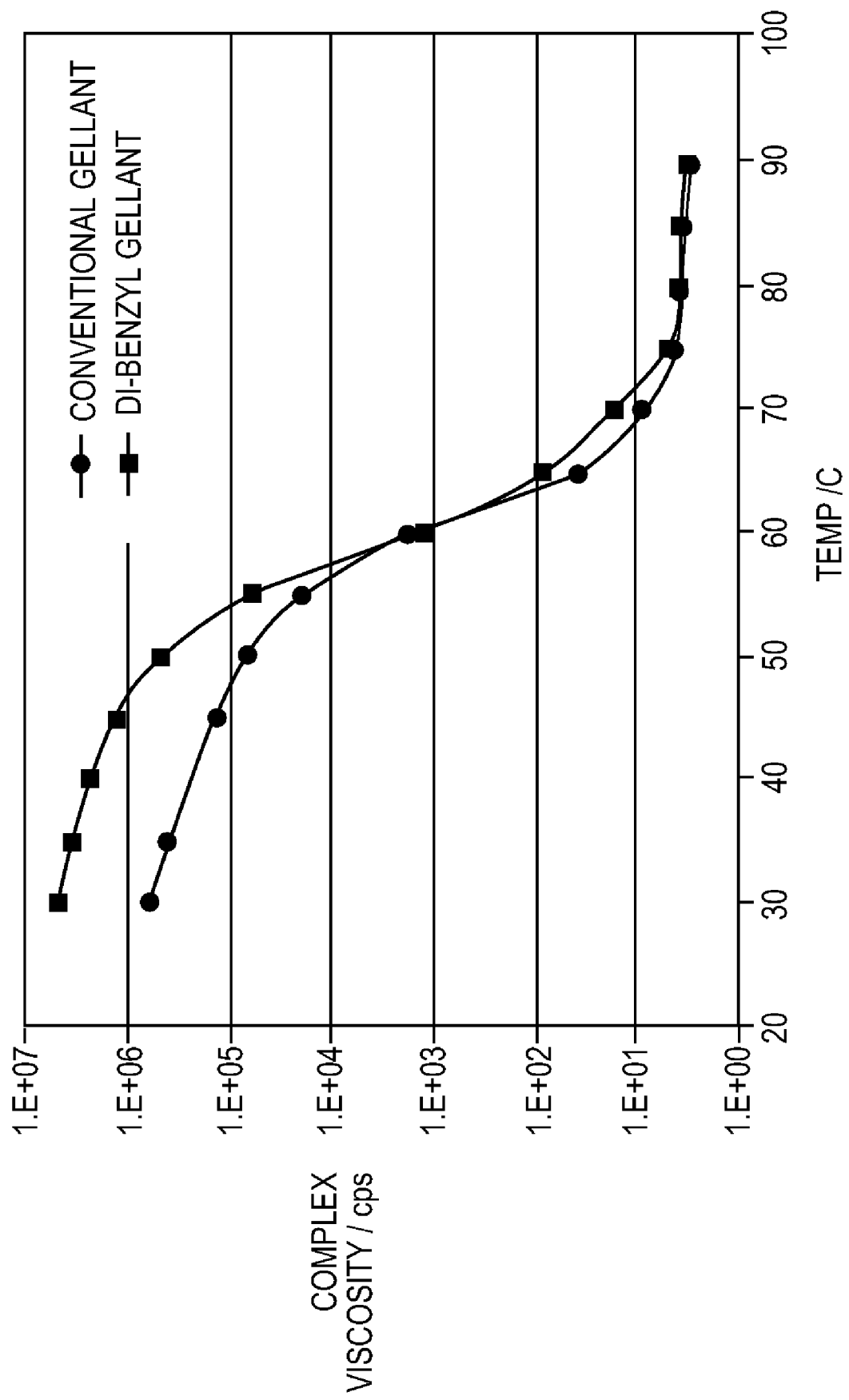
FIG. 2 is a graph showing complex viscosity (y-axis) versus temperature (x-axis) for a comparative gellant and for a di-benzyl gellant in accordance with the present disclosure.

Rheological characteristics of the gellant of Comparative Example 1 and the di-benzyl gellant of Example 3 were obtained by testing with a controlled-strain rheometer from TA Instruments (Rheometrics RFS-3). A temperature sweep from 90° C. to 30° C. at 1 Hz sweep rate was conducted with measurements every five degrees. FIG. 2 illustrates complex viscosity (y-axis, centipoise) versus temperature (x-axis, ° C.) for the gellant of Comparative Example 1 ("conventional gellant") and the di-benzyl gellant of Example 3.

Thus, in embodiments, gellant compositions comprising an organoamide of a C-36 dimer diacid having only aryl ester end groups, such as benzyl groups, and the like, provide a much simpler gellant over prior gellants which comprise more complex oligoamides having photoinitiator groups as one end-cap and caprolactone acrylate groups as the second end-cap. In embodiments, the present gellants are photoinitiator-free and exhibit lower UV-absorbance in the spectral region required for curing as compared with prior gellants. In further embodiments, the present gellants provide a more cost-effective scale-up as compared with prior gellants which required removal of many inactive side-products. In embodiments, the present oligoamide gellant derivative has only one functional moiety for the end-groups, providing a product that can be easily prepared at large scale by a simple, cost-effective process. In addition, in embodiments, it was found that the di-benzyl end-capped oligoamide gellant had significantly reduced UV absorbance in the curing spectral region, resulting in reduced UV-light energy requirements for effective curing of phase change ink prepared with the present gellants. In some embodiments, the present gellant compositions also exhibit enhanced gelating capability over prior gellants, as evidenced by the viscosity versus temperature profile. Further, the present gellant demonstrates higher thermal stability over prior gellants, which is believed to be due to the absence of a photoinitiator end-group moiety.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A compound of the formula

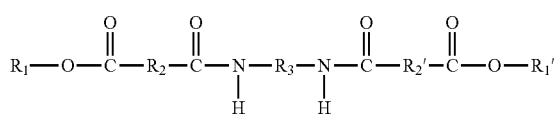

wherein R$_1$ and R$_{1'}$ can be the same or different, and wherein R$_1$ and R$_{1'}$ each, independently of the other is (i) an alkyl group having a least one ethylenic unsaturation therein, which can be linear or branched, cyclic or acyclic, and substituted or unsubstituted alkyl groups, and wherein hetero atoms may optionally be present in the alkyl group, (ii) an arylalkyl group having at least one ethylenic unsaturation therein, which can be substituted or unsubstituted arylalkyl groups, wherein the alkyl portion of arylalkyl group can be linear or branched, cyclic or acyclic, and substituted or unsubstituted, and wherein hetero atoms may optionally be present in either the aryl portion or the alkyl portion of the arylalkyl group, (iii) an alkylaryl group having at least one ethylenic unsaturation therein, which can be substituted or unsubstituted alkylaryl groups, wherein the alkyl portion of the alkylaryl group can be linear or branched, cyclic or acyclic, and substituted or unsubstituted, and wherein hetero atoms may optionally be present in either the aryl or the alkyl portion of the alkylaryl group, or (iv) an aromatic group, provided that at least one of $R_1$ and $R_{1'}$ is an aromatic group; and provided that neither of $R_1$ or $R_{1'}$ is a photo-initiator group;

wherein $R_2$ and $R_{2'}$ are the same or different, and wherein $R_2$ and $R_{2'}$ are each independently selected from (i) alkylene groups, which can be linear or branched, saturated or unsaturated, cyclic or acyclic, substituted or unsubstituted alkylene groups, and wherein hetero atoms may optionally be present in the alkylene group; (ii) arylene groups, which can be substituted or unsubstituted arylene groups, and wherein hetero atoms may optionally be present in the arylene group; (iii) arylalkylene groups, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) alkylarylene groups, which can be substituted or unsubstituted alkylarylene groups, wherein the alkyl portion of the alkylarylene group can be linear or branched, saturated or unsaturated, cyclic or acyclic, and substituted or unsubstituted, and wherein hetero atoms may optionally be present in either the aryl portion or the alkyl portion of the alkylarylene group; and wherein $R_3$ is (i) a linear or branched alkylene group, which can be saturated or unsaturated, and substituted or unsubstituted alkylene groups, and wherein hetero atoms may optionally be present in the alkylene group; (ii) an arylene group, which can be substituted or unsubstituted arylene groups, and wherein hetero atoms may optionally be present in the arylene group; (iii) an arylalkylene group, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) an alkylarylene group, which can be substituted or unsubstituted alkylarylene groups, wherein the alkyl portion of the alkylarylene group can be linear or branched, saturated or unsaturated, cyclic or acyclic, and substituted or unsubstituted, and where hetero atoms may optionally be present in either the aryl portion or the alkyl portion of the alkylarylene group.

2. The compound of claim 1, wherein one of $R_1$ or $R_{1'}$ is of the formula

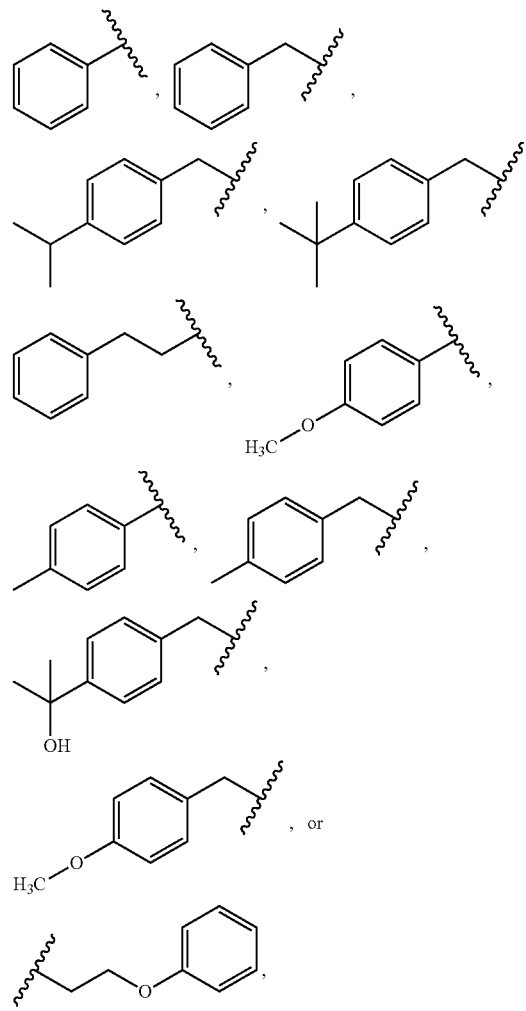

wherein ∿∿ represents the point of attachment of the $R_1$ and $R_{1'}$ group to the compound; and wherein one of $R_1$ or $R_{1'}$ is of the formula

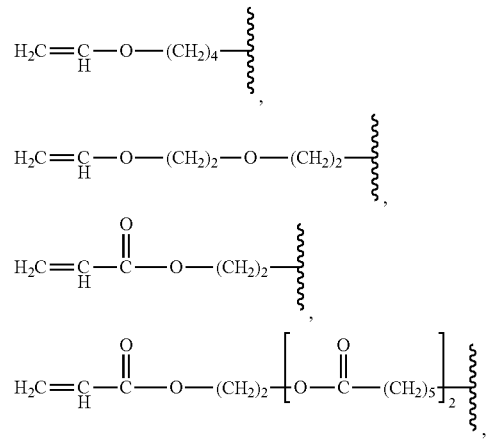

-continued

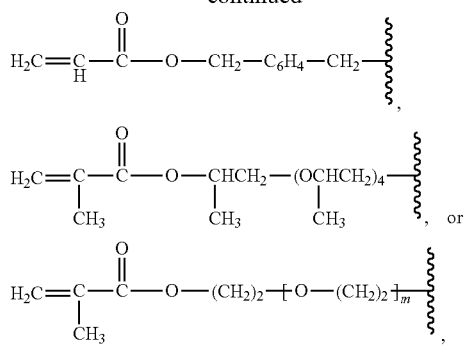

wherein m is an integer representing the number of repeating (O—(CH$_2$)$_2$ units.

3. The compound of claim 1, wherein R$_2$ and R$_{2'}$ are both alkylene groups, which can be linear or branched, saturated or unsaturated, cyclic or acyclic, and substituted or unsubstituted alkylene groups, and wherein hetero atoms may optionally be present in the alkylene group.

4. The compound of claim 1, wherein R$_2$ and R$_{2'}$ include isomers of the formula

—C$_{34}$H$_{56+a}$— and are branched alkylene groups which may include unsaturations and cyclic groups, and wherein a is an integer of 0, 1, 2, 3, 4, 5, 6, 7, 8, 9, 10, 11, or 12.

5. The compound of claim 1, wherein R$_2$ and R$_{2'}$ include isomers of the formula

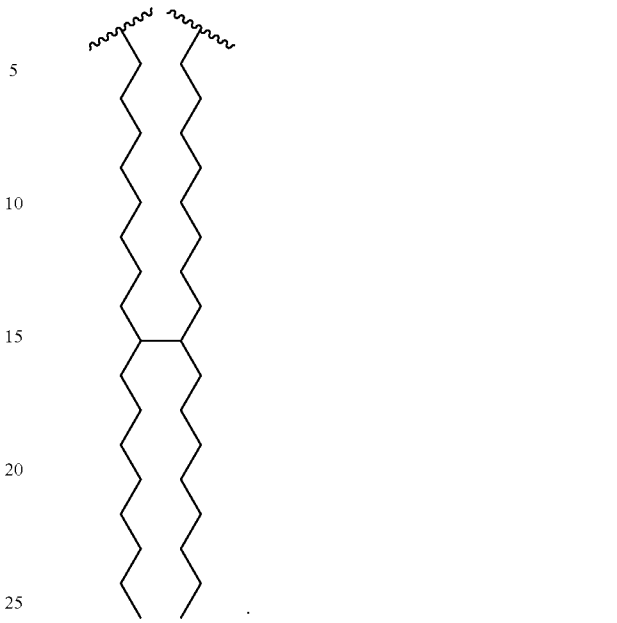

6. The compound of claim 1, wherein R$_3$ is a linear or branched alkylene group, which can be saturated or unsaturated, substituted or unsubstituted alkylene groups, and wherein hetero atoms may optionally be present in the alkylene group.

7. The compound of claim 1, wherein R$_3$ is a —CH$_2$CH$_2$—group.

8. The compound of claim 1, of the formula

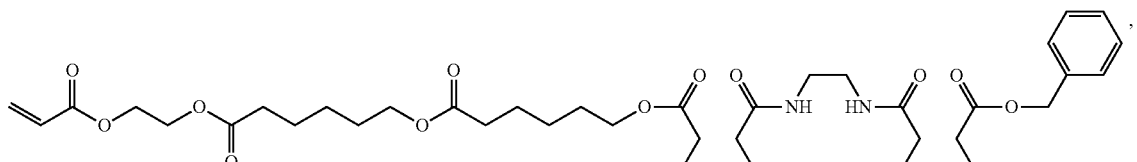

-continued

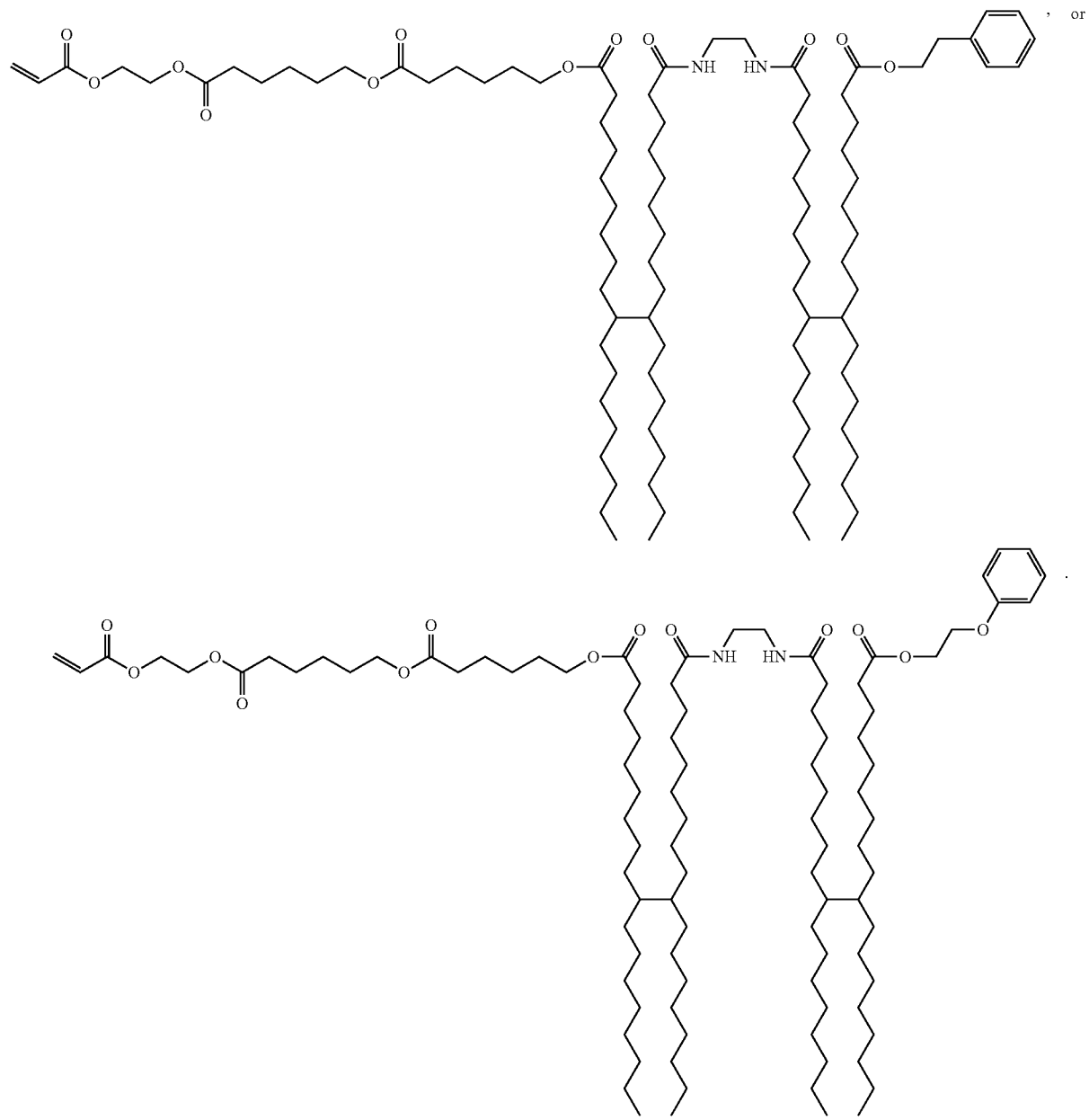

9. The compound of claim 1, wherein the compound is stable for 8 weeks in an oven held at 85° C.

10. The compound of claim 1, wherein the compound has an absorbance of from about 0 to about 0.8 at a wavelength of from about 230 to about 400 nanometers.

11. A compound of the formula

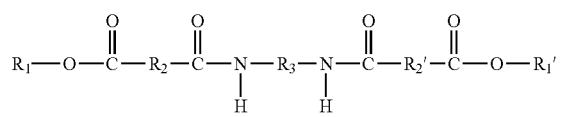

wherein $R_1$ and $R_{1'}$ are the same, and wherein $R_1$ and $R_{1'}$ are each an aromatic group;

wherein $R_2$ and $R_{2'}$ are the same or different, and wherein $R_2$ and $R_{2'}$ are each independently selected from (i) alkylene groups, which can be linear or branched, saturated or unsaturated, cyclic or acyclic, substituted or unsubstituted alkylene groups, and wherein hetero atoms may optionally be present in the alkylene group; (ii) arylene groups, which can be substituted or unsubstituted arylene groups, and wherein hetero atoms may optionally be present in the arylene group; (iii) arylalkylene groups, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) alkylarylene groups, which can be substituted or unsubstituted alkylarylene groups, wherein the alkyl portion of the alkylarylene group can be linear or branched, saturated or unsaturated, cyclic or acyclic, and substituted or unsubstituted, and wherein hetero atoms may optionally be present in either the aryl portion or the alkyl portion of the alkylarylene group; and wherein $R_3$ is (i) a linear or branched alkylene group, which can be saturated or unsaturated, and substituted or unsubstituted alkylene groups, and wherein hetero atoms may optionally be present in the alkylene group; (ii) an arylene group, which can be substituted or unsubstituted arylene groups, and wherein hetero atoms may optionally be present in the arylene group; (iii) an arylalkylene group, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) an alkylarylene group, which can be substituted or unsubstituted alkylarylene groups, wherein the alkyl portion of the alkylarylene group can be linear or branched, saturated or unsaturated, cyclic or acyclic, and substituted or unsubstituted, and where hetero atoms may optionally be present in either the aryl portion or the alkyl portion of the alkylarylene group.

12. The compound of claim 11, wherein $R_1$ and $R_{1'}$ are each of the formula

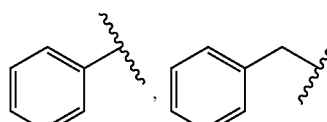

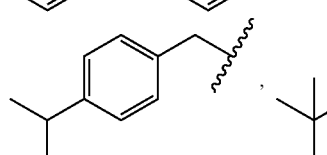

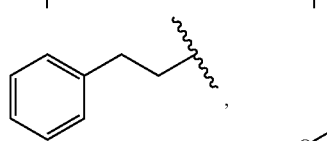

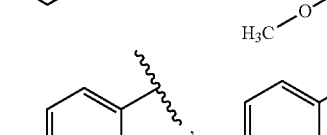

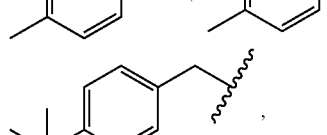

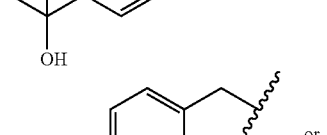

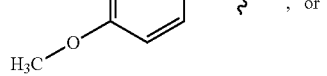, or

, wherein ~~~ represents the point of attachment of the $R_1$ and $R_{1'}$ group to the compound.

13. The compound of claim 11, wherein $R_2$ and $R_{2'}$ are both alkylene groups, which can be linear or branched, saturated or unsaturated, cyclic or acyclic, and substituted or unsubstituted alkylene groups, and wherein hetero atoms may optionally be present in the alkylene group.

14. The compound of claim 11, wherein $R_2$ and $R_{2'}$ are each groups of the formula $$-C_{34}H_{56+a}-$$

and are branched alkylene groups which may include unsaturations and cyclic groups, and wherein a is an integer of 0, 1, 2, 3, 4, 5, 6, 7, 8, 9, 10, 11, or 12.

15. The compound of claim 11, wherein $R_2$ and $R_{2'}$ include isomers of the formula

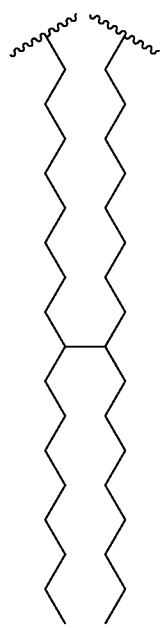

16. The compound of claim 11, wherein $R_3$ is a linear or branched alkylene group, which can be saturated or unsaturated, substituted or unsubstituted alkylene groups, and wherein hetero atoms may optionally be present in the alkylene group.

17. The compound of claim 11, wherein $R_3$ is a $$-CH_2CH_2-\text{ group.}$$

18. The compound of claim 11, of the formula
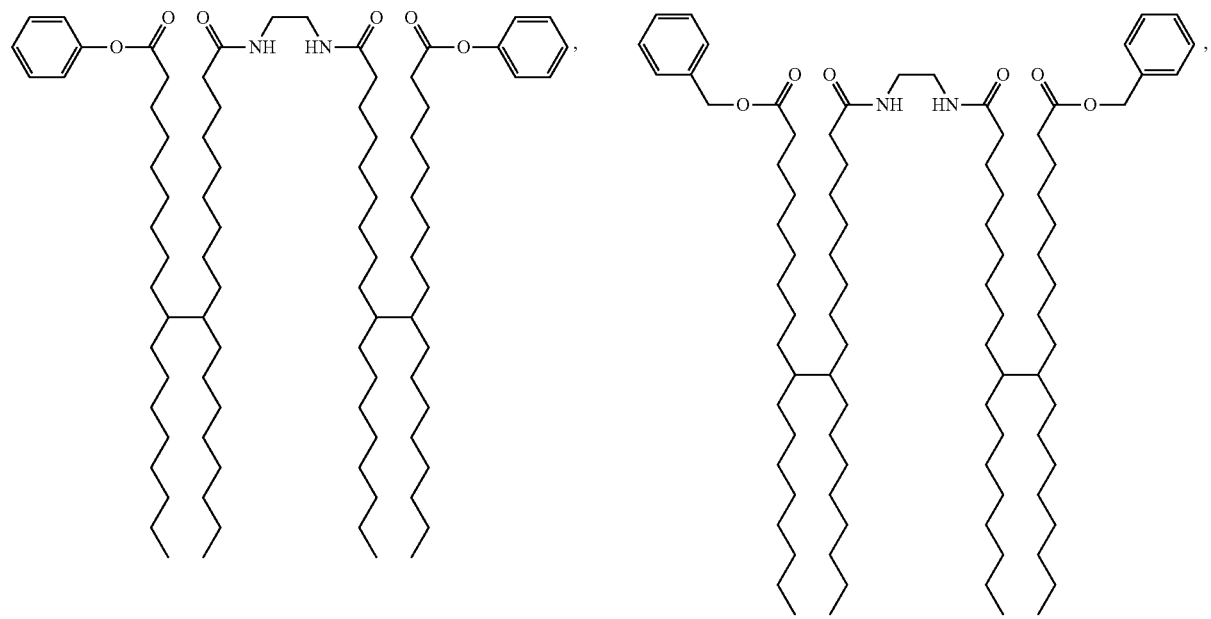
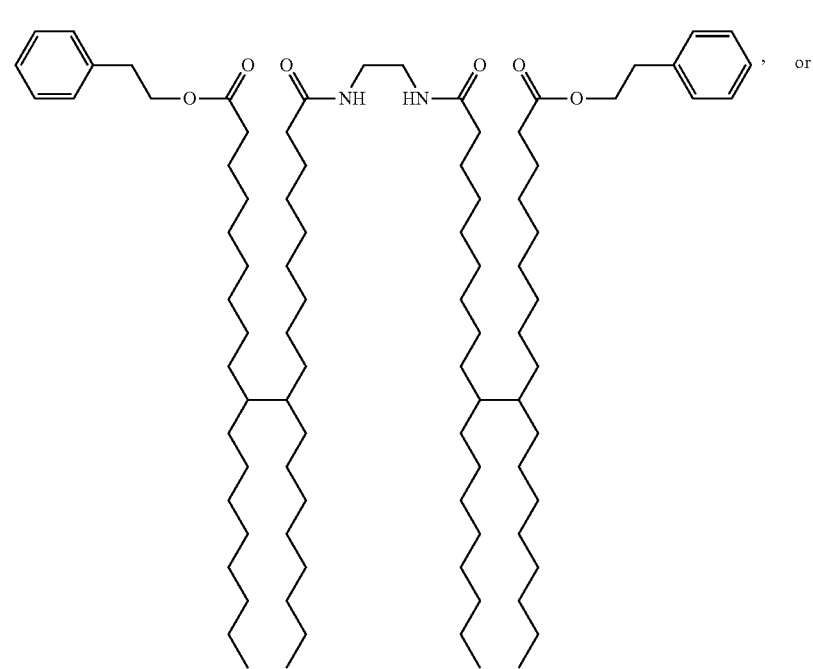

-continued
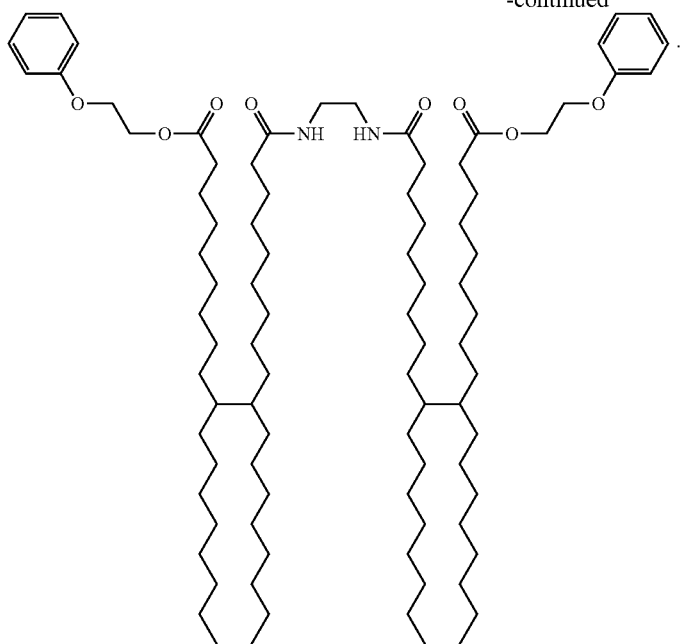
19. The compound of claim 11, wherein the compound is stable for 8 weeks in an oven held at 85° C.
20. The compound of claim 11, wherein the compound has an absorbance of from about 0 to about 0.8 at a wavelength of from about 230 to about 400 nanometers.
* * * * *